(12) United States Patent
Kishi et al.

(10) Patent No.: US 9,340,477 B2
(45) Date of Patent: May 17, 2016

(54) PROCESS FOR PRODUCTION OF HYDROXYSTILBENE DERIVATIVE HAVING PHYSIOLOGICAL ACTIVITY

(75) Inventors: Akinobu Kishi, Yamatokooriyama (JP); Satoshi Doi, Yamatokooriyama (JP); Taiji Matsukawa, Yamatokooriyama (JP); Takeki Matsui, Yamatokooriyama (JP); Yasumasa Yamada, Yamatokooriyama (JP); Ichiro Yamada, Yamatokooriyama (JP)

(73) Assignee: UHA MIKAKUTO CO., LTD., Yamatokooriyama-shi, Nara (JP)

( * ) Notice: Subject to any disclaimer, the term of this patent is extended or adjusted under 35 U.S.C. 154(b) by 270 days.

(21) Appl. No.: 13/989,920

(22) PCT Filed: Nov. 25, 2011

(86) PCT No.: PCT/JP2011/077224
§ 371 (c)(1),
(2), (4) Date: Jul. 18, 2013

(87) PCT Pub. No.: WO2012/070656
PCT Pub. Date: May 31, 2012

(65) Prior Publication Data
US 2013/0296613 A1 Nov. 7, 2013

(30) Foreign Application Priority Data

| | | |
|---|---|---|
| Nov. 26, 2010 | (JP) | 2010-264166 |
| Dec. 27, 2010 | (JP) | 2010-290547 |
| Jan. 26, 2011 | (JP) | 2011-014482 |
| Feb. 28, 2011 | (JP) | 2011-041074 |
| Mar. 25, 2011 | (JP) | 2011-068508 |
| May 26, 2011 | (JP) | 2011-118382 |
| Aug. 26, 2011 | (JP) | 2011-184539 |
| Sep. 29, 2011 | (JP) | 2011-214421 |
| Sep. 29, 2011 | (JP) | 2011-214855 |

(51) Int. Cl.

| | |
|---|---|
| C07C 39/19 | (2006.01) |
| C07C 43/23 | (2006.01) |
| C07C 41/30 | (2006.01) |
| C07C 37/16 | (2006.01) |
| A23L 1/30 | (2006.01) |
| C07C 37/14 | (2006.01) |
| C07C 39/21 | (2006.01) |

(52) U.S. Cl.
CPC ............... *C07C 39/19* (2013.01); *A23L 1/3002* (2013.01); *C07C 37/14* (2013.01); *C07C 37/16* (2013.01); *C07C 39/21* (2013.01); *C07C 41/30* (2013.01); *C07C 43/23* (2013.01)

(58) Field of Classification Search
None
See application file for complete search history.

(56) References Cited

U.S. PATENT DOCUMENTS

| | | | | |
|---|---|---|---|---|
| 8,987,522 | B2 * | 3/2015 | Shinka et al. | 568/640 |
| 2007/0197819 | A1 | 8/2007 | Hearter et al. | |
| 2008/0045752 | A1 * | 2/2008 | Sinha | C07C 37/50 568/633 |
| 2008/0286254 | A1 * | 11/2008 | Sakamoto | A23D 9/007 424/93.45 |
| 2009/0215881 | A1 * | 8/2009 | Delaire | A61K 8/375 514/441 |
| 2010/0048731 | A1 | 2/2010 | Luu et al. | |

FOREIGN PATENT DOCUMENTS

| | | |
|---|---|---|
| JP | 06-145089 A | 5/1994 |
| JP | 2001-114714 A | 4/2001 |
| JP | 2007-504191 A | 3/2007 |
| JP | 2009-528330 A | 8/2009 |
| JP | 2010-535221 A | 11/2010 |

OTHER PUBLICATIONS

Garo et al., Stilbenes from the Orchid *Phragmipedium* sp., May 2007, J. Nat. Prod., vol. 70. No. 6, pp. 968-973.*
International Search Report for PCT/JP2011/077224, mailing date of Dec. 27, 2011.

\* cited by examiner

*Primary Examiner* — Rosalynd Keys
(74) *Attorney, Agent, or Firm* — Westerman, Hattori, Daniels & Adrian, LLP

(57) ABSTRACT

A process for producing a hydroxystilbene derivative represented by formula (1) (wherein $X^1$-$X^4$ independently represent a hydrogen atom, a hydroxy group, a saturated or unsaturated linear or branched alkoxy group having 1-10 carbon atoms, or a saturated or unsaturated linear or branched alkyl group having 1-10 carbon atoms; $Z^1$ and $Z^2$ independently represent a hydrogen atom, or a group represented by the formula (2) (wherein $X^5$ and $X^6$ independently represent a hydrogen atom, a hydroxy group, a saturated or unsaturated linear or branched alkoxy group having 1-10 carbon atoms, or a saturated or unsaturated linear or branched alkyl group having 1-10 carbon atoms); and $Z^1$ and $Z^2$ may be the same as or different from each other; wherein $X^1$-$X^6$ may be the same as or different from one another), which is characterized by heating a 4-hydroxycinnamic acid compound and a hydroxystilbene compound in the presence of a metal salt.

22 Claims, 3 Drawing Sheets

PROCESS FOR PRODUCTION OF HYDROXYSTILBENE DERIVATIVE HAVING PHYSIOLOGICAL ACTIVITY

TECHNICAL FIELD

The present invention relates to a process for production of a hydroxystilbene derivative having physiological activity containing 4-hydroxycinnamic acid compounds and hydroxystilbenes as raw materials. The invention also relates to anticancer agents, anticancer agents to oral cancer, lipase inhibitors, anti-obesity agents, skin disease therapeutic agents, foods, pharmaceutical agents, quasi-drugs, and cosmetics containing the hydroxystilbene derivative. The invention also relates to a novel hydroxystilbene derivative.

BACKGROUND ART

The 4-hydroxycinnamic acid compounds are secondary metabolites biosynthesized in plants mainly in the shikimic acid pathway and are compounds serving as raw materials of substances whose physiological activity have been reported in a large number of reports, such as phenyl propanoid, flavonoid, lignan, and tannin. The 4-hydroxycinnamic acid compounds themselves are also compounds which are biosynthesized from plants in order to protect the plants themselves and seeds from ultraviolet rays and a large amount of which are present in the nature. With respect to flavonoid, lignan, and the like which are polymers of the 4-hydroxycinnamic acid compounds, a large number of compounds having physiological activity are present and foods containing the same are eaten for health enhancement.

The hydroxystilbenes are secondary metabolites biosynthesized in the shikimic acid pathway in plants. For example, resveratrol, piceatannol, pterostilbene, and the like are mentioned. The physiological activities thereof have been reported in a large number of reports and they are compounds which draw particularly high attention. The hydroxystilbenes are contained in grapes and berries in a relatively high proportion and a large number of foods, supplements, and the like containing the same are commercially available. Polymers thereof are similarly contained but the content thereof is very small, and thus physiological activity cannot be expected.

As the 4-hydroxycinnamic acid compounds and derivatives of hydroxystilbenes, substances are hardly mentioned except polymers. As the hydroxystilbene derivative, alkylether and ester phosphate have been merely examined (Patent Document 1).

With respect to hydroxystilbene, flavonoid, lignan, and the like, various physiological activities have been reported. However, purifying the compounds from natural products poses a large number of problems in terms of cost and working efficiency. Further, a large amount of trace constituents are included. Therefore, a process for easily obtaining the same has been desired.

CITATION LIST

Patent Literature

Patent Document 1: Japanese Unexamined Patent Application Publication (Translation of PCT Application) No. 2010-535221

SUMMARY OF INVENTION

Technical Problem

In view of the above-described circumstances, the present inventors have conducted extensive researches in order to establish a process for production of a hydroxystilbene derivative. As a result, the present inventors have successively produced a hydroxystilbene derivative excellent in physiological activities, such as anti-cancer activity, anti-cancer activity to oral cancer, and lipase inhibition activity, by a simple and safe process including heating 4-hydroxycinnamic acid compounds and hydroxystilbenes as the raw materials in the presence of a metal salt, and thus have accomplished the present invention.

Therefore, it is an object of the present invention to provide a process for efficiently and safely obtaining a hydroxystilbene derivative having one or more kinds of physiological activities of anti-cancer activity, anti-cancer activity to oral cancer, and lipase inhibition activity.

It is another object of the present invention to provide anticancer agents, anticancer agents to oral cancer, lipase inhibitors, anti-obesity agents, skin disease therapeutic agents, foods, pharmaceutical agents, quasi-drugs, and cosmetics containing the hydroxystilbene derivative.

It is still another object of the present invention to provide a novel hydroxystilbene derivative having one or more kinds of physiological activities of anti-cancer activity, anti-cancer activity to oral cancer, and lipase inhibition activity.

Solution to Problem

The gist of the invention relates to the following items:

[1] A process for producing a hydroxystilbene derivative represented by Formula (1):

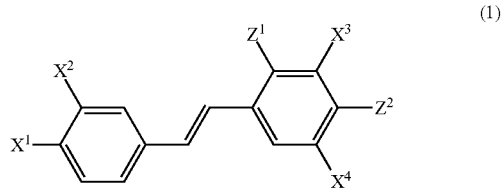

(in Formula (1), $X^1$-$X^4$ independently represent a hydrogen atom, a hydroxy group, a saturated or unsaturated linear or branched alkoxy group having 1-10 carbon atoms, or a saturated or unsaturated linear or branched alkyl group having 1-10 carbon atoms; $Z^1$ and $Z^2$ independently represent a hydrogen atom or a group represented by Formula (2):

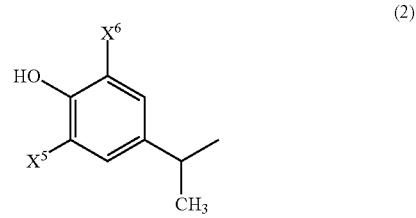

(in Formula (2), $X^5$ and $X^6$ independently represent a hydrogen atom, a hydroxy group, a saturated or unsaturated linear or branched alkoxy group having 1-10 carbon atoms, or a saturated or unsaturated linear or branched alkyl group having 1-10 carbon atoms); and $Z^1$ and $Z^2$ may be the same or different from each other; in which $X^1$-$X^6$ may be the same or different from one another), the process being characterized by heating 4-hydroxycinnamic acid compounds and hydroxystilbene in the presence of a metal salt.

[2] An anticancer agent containing a hydroxystilbene derivative produced by the process described above,

[3] An anticancer agent to oral cancer containing a hydroxystilbene derivative produced by the process described above,

[4] A lipase inhibitor containing a hydroxystilbene derivative produced by the process described above,

[5] An anti-obesity agent containing a hydroxystilbene derivative produced by the process described above,

[6] A skin disease therapeutic agent containing a hydroxystilbene derivative produced by the process described above,

[7] A food, a pharmaceutical agent, a quasi-drug, or cosmetics containing a hydroxystilbene derivative produced by the process described above, and

[8] A novel physiologically active hydroxystilbene derivative or a pharmacologically permissible salt thereof represented by Formula (5):

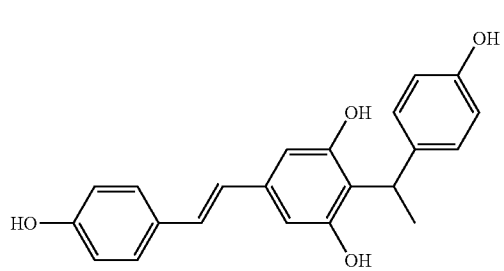

Formula (6):

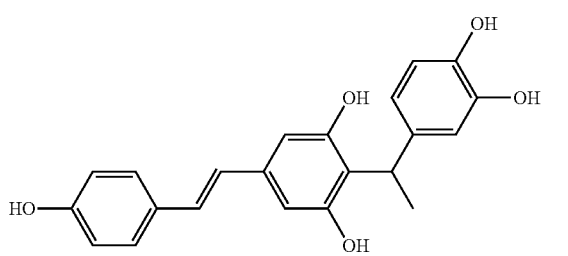

Formula (7):

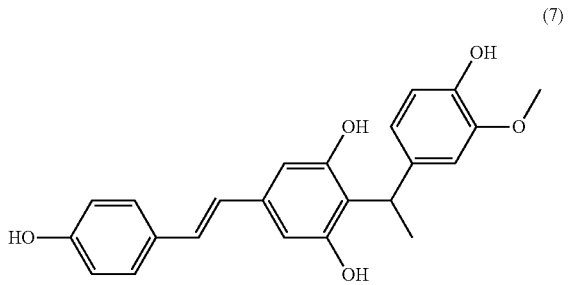

Formula (8):

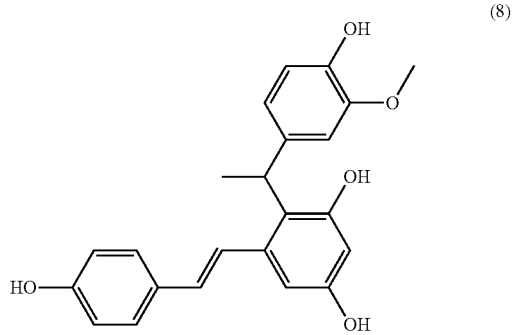

Formula (9):

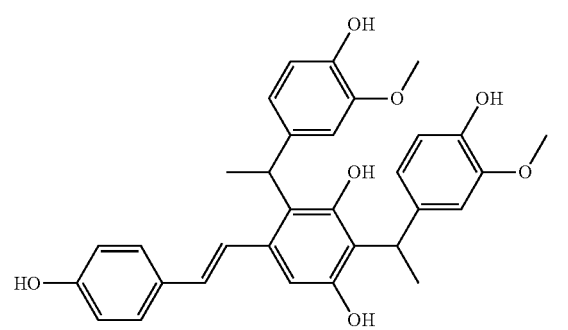

Formula (10):

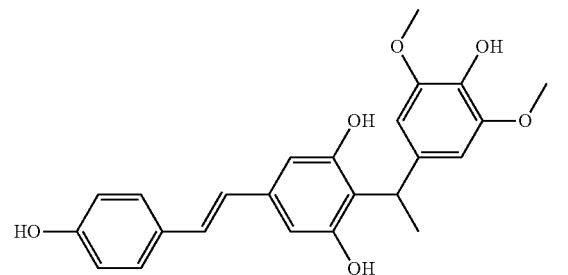

Formula (11):

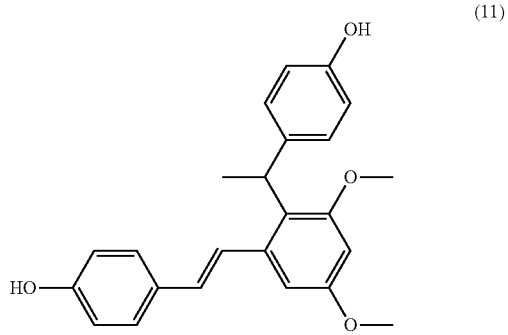

Formula (12):

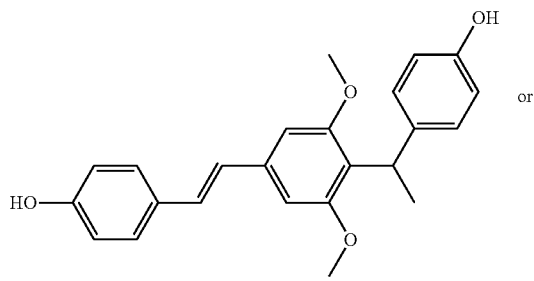

or

Formula (13):

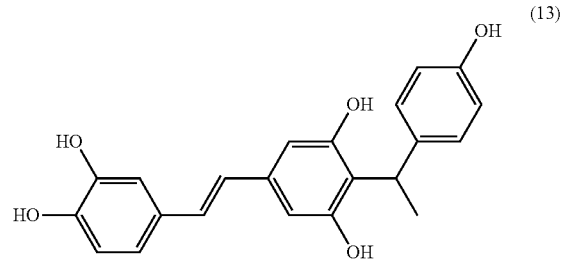

Advantageous Effects of Invention

According to the present invention, a hydroxystilbene derivative excellent in physiological activities, such as anti-cancer activity, anti-cancer activity to oral cancer, and lipase inhibition activity, can be efficiently and safely obtained.

The hydroxystilbene derivative obtained by the invention also serves as an active ingredient of anticancer agents, anti-cancer agents to oral cancer, lipase inhibitors, anti-obesity agents, and skin disease therapeutic agents and also, by compounding the hydroxystilbene derivative in foods, pharmaceutical agents, quasi-drugs, or cosmetics, the physiological activities can be newly imparted to these products or the physiological activities which are already imparted thereto can be further strengthened.

DESCRIPTION OF EMBODIMENTS

Figure 1:
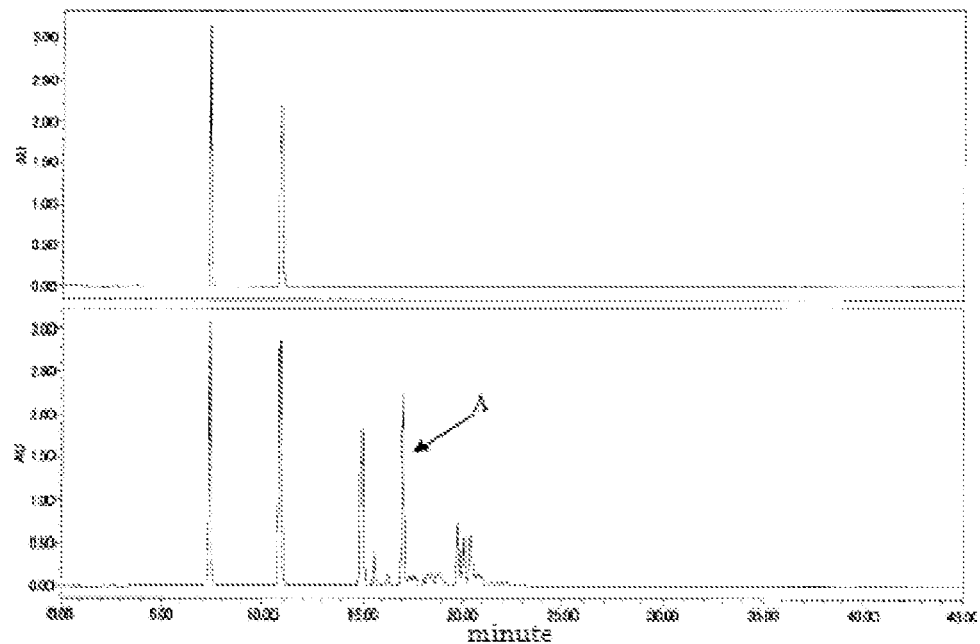
FIG. 1 show analysis results of high performance liquid chromatography (HPLC) performed in Example 1. The upper view shows the results before a reaction and the lower view shows the results after a reaction, in which "A" represents peak of a hydroxystilbene derivative generated using resveratrol and p-coumaric acid as raw materials.

Hereinafter, the invention is described in detail.

The invention is a process for production of a hydroxystilbene derivative having physiological activity including a process for heating one or more kinds of 4-hydroxycinnamic acid compounds and one or more kinds of hydroxystilbenes in the presence of a metal salt.

In the invention, the physiological activities refer to anti-cancer activity, anti-cancer activity to oral cancer, and lipase inhibition activity. A compound having one or more of the physiological activities is referred to as a "compound having physiological activity".

In the production process of the invention, 4-hydroxycinnamic acid compounds are used as the raw materials. The 4-hydroxycinnamic acid compounds may be a cinnamic acid compound having a hydroxyl group at the 4th position of the benzene portion and a derivative thereof. Specifically, compounds represented by the following formula (3) are given.

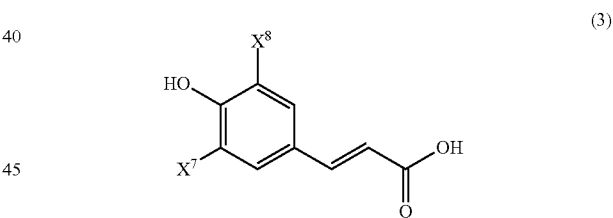

(in Formula (3), $X^7$ and $X^8$ independently represent a hydrogen atom, a hydroxy group, a saturated or unsaturated linear or branched alkoxy group having 1-10 carbon atoms, or a saturated or unsaturated linear or branched alkyl group having 1-10 carbon atoms, and $X^7$ and $X^8$ may be the same or different from each another.)

As the 4-hydroxycinnamic acid compounds, a 4-hydroxycinnamic acid compound having hydrogen at the 2nd position and the 6th position of the benzene portion and having the same functional group or different functional groups selected from hydrogen, a hydroxy group, a saturated or unsaturated linear or branched alkoxy group having 1-10 carbon atoms, and a saturated or unsaturated linear or branched alkyl group having 1-10 carbon atoms at the 3rd position and the 5th position of the benzene portion is preferable from the viewpoint of good generation efficiency during a reaction. From the view point of availability and cost, p-coumaric acid, ferulic acid, caffeic acid, sinapic acid, di-t-butyl hydroxycinnamic acid, artepillin C, and the like are more preferable.

Moreover, in the production process of the invention, hydroxystilbenes are used as the raw materials. The hydroxystilbenes may be stilbenes having one or more hydroxyl groups. Specifically, compounds represented by the following formula (4) are given.

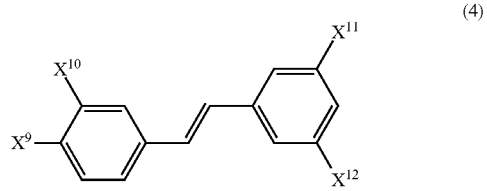

(in Formula (4), $X^9$-$X^{12}$ independently represent a hydrogen atom, a hydroxy group, a saturated or unsaturated linear or branched alkoxy group having 1-10 carbon atoms, or a saturated or unsaturated linear or branched alkyl group having 1-10 carbon atoms and $X^9$-$X^{12}$ may be the same or different from one another.) In particular, from the viewpoint of availability and cost, resveratrol, piceatannol, pterostilbene, and the like are more preferable.

In the production process of the invention, a hydroxystilbene derivative having a desired structure can be obtained by selecting the kind of the 4-hydroxycinnamic acid compounds and the hydroxystilbenes as described later.

The 4-hydroxycinnamic acid compounds as the raw materials may be those derived from nature or chemical products with high purity which are obtained by chemical synthesis. The naturally derived 4-hydroxycinnamic acid compounds are not required to be completely purified and a mixture containing the ingredients of the 4-hydroxycinnamic acid compounds can be also used. The 4-hydroxycinnamic acid compounds include derivatives, such as salts and esters. In the production process of the invention, these derivatives can be also used as the raw materials.

As the derivatives of the 4-hydroxycinnamic acid compounds, salts, such as sodium salt, potassium salt, and calcium salt, and esters, such as methyl ester and ethyl ester, are given.

From the viewpoint of increasing the generation efficiency and the recovery rate of the hydroxystilbene derivative, a mixture containing the 4-hydroxycinnamic acid compounds in a proportion of 10% by weight or more in total is preferable as the raw materials.

The hydroxystilbenes as the raw materials may be those derived from nature or chemical products with high purity which are obtained by chemical synthesis. The naturally-derived hydroxystilbenes are not required to be completely purified and a mixture containing the ingredients of the hydroxystilbenes can be also used. The hydroxystilbenes include salts. In the production process of the invention, the derivatives can be also used as the raw materials.

As the derivatives of the hydroxystilbenes, salts, such as sodium salt, potassium salt, and calcium salt, are given.

From the viewpoint of increasing the generation efficiency and the recovery rate of the hydroxystilbenes, a mixture containing the hydroxystilbenes in a proportion of 5% by weight or more in total is preferable as the raw materials.

In the production process of the invention, the 4-hydroxycinnamic acid compounds and the hydroxystilbenes are dissolved in a suitable solvent. In this case, when the solvent contains only water, the 4-hydroxycinnamic acid compounds and the hydroxystilbenes may be dissolved in a mixed liquid of water and an organic solvent or only an organic solvent because the solubility of the 4-hydroxycinnamic acid compounds and the hydroxystilbenes in water is remarkably low. In this case, the compounding ratio of water and the organic solvent and the kind of the organic solvent are not particularly limited insofar as the 4-hydroxycinnamic acid compounds and the hydroxystilbenes are sufficiently dissolved. In particular, the use of a solvent containing only methanol or only ethanol or a mixed liquid of water and methanol or a mixed liquid of water and ethanol is preferable in terms of safety and cost. When using a composition (reactant) containing the hydroxystilbene derivative after the reaction for foods without sufficiently purifying the same, it is preferable to use ethanol or hydrous ethanol as the solvent in terms of safety, and laws and regulations.

The concentration of the 4-hydroxycinnamic acid compounds and the hydroxystilbenes in the solution containing the 4-hydroxycinnamic acid compounds and the hydroxystilbenes obtained as described above is not particularly limited. For example, when the concentration of the 4-hydroxycinnamic acid compounds and the hydroxystilbenes is higher, there are merits such that the use amount of the solvent is small. Therefore, it is preferable to adjust the concentration of the 4-hydroxycinnamic acid compounds and the hydroxystilbenes in such a manner as to be close to the concentration at which they are saturated in each solvent.

In the production process of the invention, in order to react the 4-hydroxycinnamic acid compounds and the hydroxystilbenes to obtain the target hydroxystilbene derivative, a metal salt is added to a solution containing the 4-hydroxycinnamic acid compounds and the hydroxystilbenes (hereinafter referred to as a raw material solution).

In the production process of the invention, the reaction of generating the hydroxystilbene derivative proceeds even under acidic conditions or alkaline conditions insofar as the reaction proceeds in the presence of a metal salt.

However, when the raw materials are compounds having two or more hydroxyl groups adjacent to each other in the benzene portion, such as caffeic acid, trihydroxycinnamic acid, or piceatannol, a decomposition reaction, a reaction of hydroxystilbenes, and a reaction of 4-hydroxycinnamic acid compounds are likely to proceed in the case of alkaline conditions, and the recovery rate of the hydroxystilbene derivative which is the target compound decreases in some cases.

Accordingly, when hydroxycinnamic acid compounds and hydroxystilbenes having two or more hydroxyl groups adjacent to each other in the benzene portion, such as caffeic acid, trihydroxycinnamic acid, and piceatannol, are contained as the raw materials or when the hydroxystilbene derivative is targeted, the pH of the raw material solution when starting the reaction is desirably lower than 7. In the invention, the conditions where the pH is lower than 7 are acidic conditions and the conditions where the pH is 7 or higher are alkaline conditions.

However, it is desirable to appropriately select the reaction conditions considering the intended use of the hydroxystilbene derivative to be obtained and the presence or absence of purifying operation and isolation operation and, when added to foods, considering the taste and the like.

The metal salt may be any one of acidic salts, basic salts, and normal salts and may be any one of single salts, double salts, and complex salts. The metal salt may be one kind thereof or a mixture of two or more kinds thereof. As an example of the metal salt, one approved as food additives is preferable in terms of safety. For example, magnesium salt, calcium salt, sodium salt, potassium salt, zinc salt, copper salt, and the like which are approved to be added to foods are given.

The mixture of the metal salts includes, for example, a mixture containing several kinds of metal salts, such as Mineral premix (Tanabe Seiyaku Co., Ltd., mineral mixture containing zinc gluconate, iron ammonium citrate, calcium lactate, copper gluconate, and magnesium phosphate as the main ingredients). Moreover, mineral water can be also mentioned as the mixture containing a plurality of kinds of metal salts.

The content of the metal salt in the raw material solution is not particularly limited insofar as the hydroxystilbene derivative can he generated.

Next, the raw material solution is heated in the presence of a metal salt. By the heating treatment, the generation reaction of the target hydroxystilbene derivative is performed. In order to efficiently advance the generation reaction, the heating temperature of the raw material solution is preferably adjusted to 90° C. or higher. Considering the boiling point of the solvent to be used, it is preferable to perform pressurization and heating. It is preferable to heat the solution in such a manner that the solution temperature at least partially reaches 90° C. or higher by, for example, placing the raw material solution in an open container, and then heating the container at a high temperature exceeding the boiling point of the solvent, placing the raw material solution in an airtight container, heating the container, and performing pressurization and heating using a retort apparatus or an autoclave, and the like. It is still more preferable that the solution temperature uniformly becomes 90° C. to 150° C. in terms of increasing the generation efficiency and the recovery efficiency of the target hydroxystilbene derivative. The heating time is not limited similarly as the heating temperature and the time conditions may be determined in such a manner that the target reaction efficiently proceeds. In particular, the heating time depends on the balance of the heating temperature and the solvent amount. The heating time is desirably set according to the heating temperature and the solvent amount. For example, when the raw material solution is heated around 130° C., the heating is preferably performed for 5 minutes to 24 hours after the solution temperature reaches 130° C. The heating may be performed once or may be repeatedly performed in a plurality of stages. When the heating is performed in a plurality of stages, it is preferable to perform the heating after newly adding only a solvent or a solvent containing a metal salt.

The completion of the generation reaction of the hydroxystilbene derivative by the heating may be judged, for example by confirming the generation amount of the hydroxystilbene derivative by the componential analysis by HPLC described in Examples below.

The hydroxystilbene derivative manufactured by the production process of the invention is a compound represented by Formula (1):

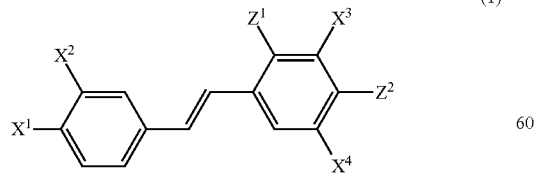

(1)

(in Formula (1), $X^1$-$X^4$ independently represent a hydrogen atom, a hydroxy group, a saturated or unsaturated linear or branched alkoxy group having 1-10 carbon atoms, or a saturated or unsaturated linear or branched alkyl group having 1-10 carbon atoms; $Z^1$ and $Z^2$ independently represent a hydrogen atom or a group represented by Formula (2):

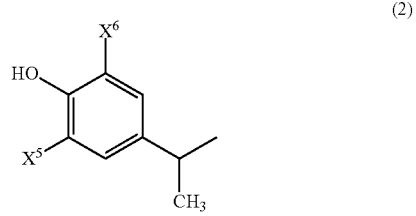

(2)

(in Formula (2), $X^5$ and $X^6$ independently represent a hydrogen atom, a hydroxy group, a saturated or unsaturated linear or branched alkoxy group having 1-10 carbon atoms, or a saturated or unsaturated linear or branched alkyl group having 1-10 carbon atoms); and $Z^1$ and $Z^2$ may be the same or different from each other; in which $X^1$-$X^6$ may be the same or different from one another).

The compound represented by Formula (1) includes compounds represented by Formula (5):

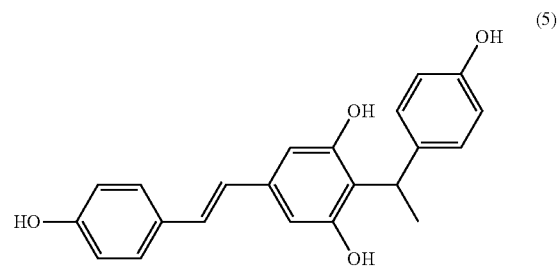

(5)

Formula (6):

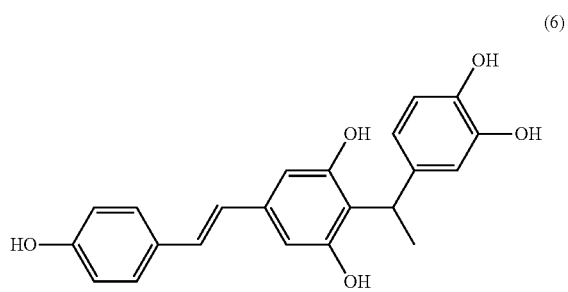

(6)

Formula (7):

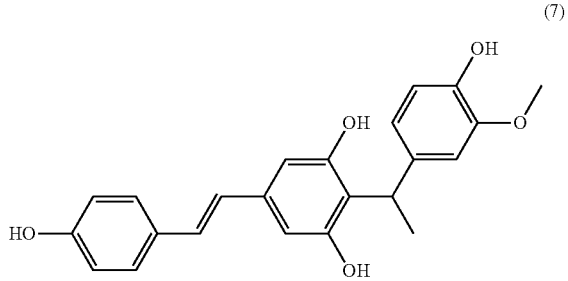

(7)

Formula (8):

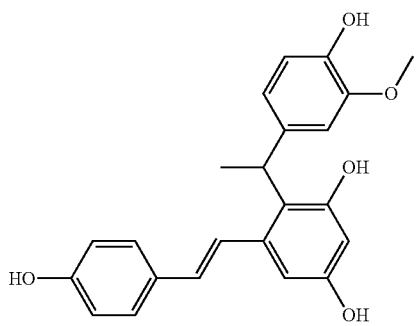

(8)

Formula (9):

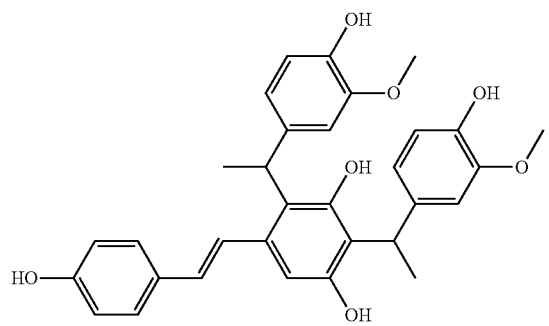

(9)

Formula (10):

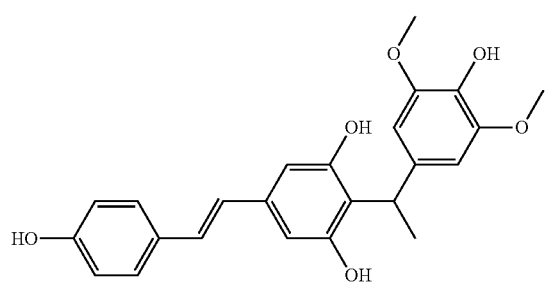

(10)

Formula (11):

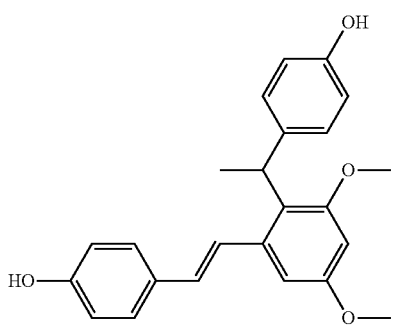

(11)

Formula (12):

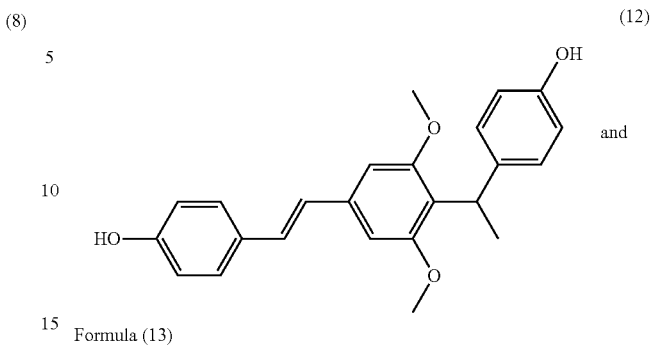

(12)

and

Formula (13)

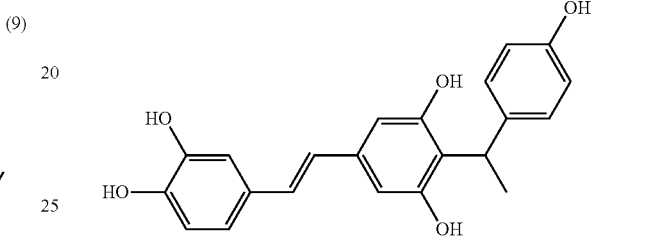

(13)

As the hydroxystilbene derivative generated by the production process of the invention, pharmacologically permissible salts are included.

The pharmacologically permissible salts include, for example, alkaline metal salts, such as lithium salt, sodium salt, and potassium salt; alkaline earth metal salts, such as magnesium salt, calcium salt, and barium salt; aluminum salt; metal hydroxide salts, such as aluminum hydroxide salt; amine salts, such as alkyl amine salt, dialkylamine salt, trialkylamine salt, alkylene diamine salt, cycloalkyl amine salt, aryl amine salt, aralkyl amine salt, and heterocyclic amine salt; amino acid salts, such as α-amino acid salt and ω-amino acid salt; peptide salt or primary, secondary, tertiary, or quaternary amine salts derived therefrom. These pharmacologically permissible salts can be used singly or as a mixture of two or more kinds thereof.

As processes for efficiently producing the hydroxystilbene derivatives represented by Formulae (5) to (13), the following processes are given.

(1) By heating resveratrol and p-coumaric acid in the presence of a metal salt (preferably acidic), the compound represented by Formula (5) can be produced.

(2) By heating resveratrol and caffeic acid in the presence of a metal salt (preferably acidic), the compound represented by Formula (6) can be produced.

(3) By heating resveratrol and ferulic acid in the presence of a metal salt (preferably acidic), the compound represented by Formula (7), Formula (8), or Formula (9) can be produced.

(4) By heating resveratrol and sinapic acid in the presence of a metal salt (preferably acidic), the compound represented by Formula (10) can be produced.

(5) By heating pterostilbene and p-coumaric acid in the presence of a metal salt (preferably acidic), the compound represented by Formula (11) or Formula (12) can be produced.

(6) By heating piceatannol and p-coumaric acid in the presence of a metal salt (preferably acidic), the compound represented by Formula (13) can be produced.

When the hydroxystilbene derivative is produced in the process only using safe materials, the hydroxystilbene derivative can be used for foods, pharmaceutical agents, quasi-drugs, or cosmetics in a state of a mixture containing the hydroxystilbene derivative. For example, when naturally-derived 4-hydroxycinnamic acid compounds and hydroxystilbenes are dissolved in a hydrous ethanol solvent, and heated using mineral water or mineral premix, the liquefied reactant to be obtained can be used as one of food raw materials.

When an improvement of flavor and higher functionality are desired, the concentration of the hydroxystilbene derivative is increased by condensing the reactant or a pure article of the hydroxystilbene derivative can be obtained by purifying the reactant. The condensing and the purification can be carried out by known methods. For example, the hydroxystilbene derivative can be condensed by extracting by methods such as solvent extraction methods with chloroform, ethyl acetate, ethanol, methanol, and the like, a supercritical extraction method with carbon dioxide gas, and the like. Moreover, the condensing and the purification can be also carried out utilizing column chromatography. For the condensing and the purification, a recrystallization method and a membrane treatment method with an ultrafiltration membrane or the like can be also used.

When isolating the hydroxystilbene derivative from the reactant and collecting the same, column chromatography, HPLC, and the like may be used.

By subjecting the condensed substance or the purified substance to drying under reduced pressure or freeze-drying as required to remove the solvent, a powdery solid can be obtained.

A further effect and efficacy of the hydroxystilbene derivative obtained by the invention can be used in the range which is analogized from the obtained physiological activity data.

Since the safety of the 4-hydroxycinnamic acid compounds and hydroxystilbenes which are the raw materials to be used in the invention and also a solvent, a metal salt, and the like to be used for the generation are already generally confirmed, it is considered that the safety of the hydroxystilbene derivative obtained by the invention is also similarly excellent.

The hydroxystilbene derivative has one or more physiological activities, such as anti-cancer activity, anti-cancer activity to oral cancer, and lipase inhibition activity, as described in Examples described later.

Accordingly, the hydroxystilbene derivative can be used as an active ingredient of anticancer agents, anticancer agents for oral cancer, lipase inhibitors, and the like. Moreover, the hydroxystilbene derivative having lipase inhibition activity can be used as an active ingredient of anti-obesity agents or skin disease therapeutic agents.

The hydroxystilbene derivative can be compounded in foods, pharmaceutical agents, quasi-drugs, cosmetics, and the like for use.

The foods may be in any form, such as beverages, alcoholic beverages, jellies, confectioneries, and the like, for example. Among the confectionaries, a hard candy, a soft candy, a gummi candy, a tablet, and the like which are excellent in storageability or portability from the capacity and the like are given as examples but the confectionaries are not particularly limited thereto. The foods also include functional foods, health foods, health-conscious foods, and the like.

The pharmaceutical agents include solid preparations, such as powder agents, tablets, pills, capsule agents, fine grain agents, and granule agents; liquid agents, such as water agents, suspension agents, and emulsion agents; gel agents, and the like. The tablets, pills, granule agents, and granules in capsule agents may be sugar-coated with sugars, such as sucrose, and sugar alcohols, such as maltitol, coated with gelatin, hydroxypropyl cellulose, hydroxypropyl methylcellulose, and the like, or covered with a film of a gastric-soluble substance or an enteric-soluble substance, as required. The pharmaceutical agents mentioned above can be also subjected to known solubilization treatment in order to increase the solubility of the pharmaceuticals. The liquid agents may be compounded in injection agents and drop agents for use based on a usual method.

The quasi-drugs include are toothpastes, mouthwashes, mouse rinses, nutrients, and the like.

The cosmetics include lotions, milky lotions, creams, facial mask agents, finishing cosmetics, hair care products, face washing agents, bath agents, antiperspirants, and the like. With respect to the cosmetics, a recovery from pimples is expected from the lipase inhibition effect, and the cosmetics can be utilized for the purpose of prevention of pimples and recovery from pimples.

When preparing foods, pharmaceutical agents, quasi-drugs, or cosmetics using the hydroxystilbene derivative, ingredients usually used for foods, pharmaceutical agents, quasi-drugs, or cosmetics can be compounded as appropriate in the range where the effects of the invention are not impaired.

For example, in the case of foods, the hydroxystilbene derivative can be combined with raw materials or materials usually compounded in foods, such as water, alcohol, starch, protein, fiber, sugar, lipid, vitamin, mineral, a flavoring agent, a colorant, a sweetener, a seasoning, a stabilizer, and an antiseptic agent.

In the case of pharmaceutical agents, quasi-drugs, or cosmetics, the hydroxystilbene derivative is combined with a main agent, a base material, a surfactant, a foaming agent, a moisturizing agent, a thickening agent, a clearing agent, a flavoring agent, a colorant, a stabilizer, an antiseptic agent, a disinfectant, and the like, and can be prepared into the form of a liquid, an ointment, the final form which can be spray ejected, and the like based on a usual method.

When adding the hydroxystilbene derivative to foods, it is usually preferable to add the same into the foods in a proportion of 0.001 to 20% by weight.

When the hydroxystilbene derivative is used for medical application, the intake, for example, is not particularly limited insofar as a desired improvement effect, a desired medical treatment effect, or a desired preventive effect is obtained and is usually selected as appropriate according to the aspect thereof, the age, sex, physical constitution, other conditions of patients, and the kind and extent of diseases, and the like. The intake may be about 0.1 mg to about 1,000 mg per day and can be divided into 1 to 4 doses per day.

When adding the hydroxystilbene derivative to quasi-drugs or cosmetics, it is usually preferable to add the same into the quasi-drugs or the cosmetics in a proportion of 0.001 to 30% by weight.

Since the hydroxystilbene derivative is excellent in safety, the hydroxystilbene derivative may be used not only for human beings and may be compounded in therapeutic agents or feed for nonhuman animals, such as mammals, such as rats, mice, guinea pigs, rabbits, sheep, pigs, cows, horses, cats, dogs, apes, and chimpanzees, birds, amphibians, and reptiles. The feed includes, for example, cattle feeds for sheep, pigs, cows, horses, chickens, and the like, feeds for small animals for rabbits, rats, mice, and the like, feeds for fish and shellfishes for eels, sea breams, yellowtails, shrimps, and the like, and pet foods for dogs, cats, caged little birds, squirrels, and the like.

Next, the invention is described in detail with reference to Examples but the invention is not limited only to the Examples.

EXAMPLES

Example 1

Generation of Hydroxystilbene Derivative from Resveratrol and p-coumaric Acid 1 g of trans-resveratrol (manufactured by Tokyo Chemical Industry Co., Ltd.) and 1 g of p-coumaric acid (manufactured by Wake Pure Chemical Industries, Ltd.) were dissolved in 20 mL of ethanol, and then 20 mL of mineral water (Trade name "Gerolsteiner", manufactured by Sapporo Beverage, Ltd.) was added, thereby obtaining a solution (pH=4.6) containing resveratrol and p-coumaric acid. The solution containing resveratrol and p-coumaric acid was heated at 130° C. for 90 minutes in an autoclave ("SANYO LABO AUTOCLAVE" manufactured by SANYO Electric Co., Ltd., which was used in the following Examples). 1 mL of the obtained reactant solution was diluted with methanol in a measuring cylinder to 50 mL, and then analyzed by HPLC.

The HPLC analysis was performed under the following conditions.
Column: Negative-phase column "Develosil (Registered Trademark) C-30-UG-5" (4.6 mmi.d.×250 mm)
Mobile phase: A—$H_2O$ (0.1% trifluoroacetic acid (TFA)), B—Acetonitrile (0.1% TFA)
Flow velocity: 1 mL/min
Pouring: 10 μL
Detection: 254 nm
Gradient (% by capacity): From 80% A/20% B to 20% A/80% B for 30 minutes, From 20% A/80% B to 100% B for 5 minutes, 100% B for 10 minutes (all straight line)

The obtained chromatograms are shown in FIG. 1. The upper view shows the chromatogram before the generation reaction and the lower view shows the chromatogram after the generation reaction. As shown in the lower view, it was confirmed that a plurality of compounds are generated including the peak A.

Example 2

Isolation and Structural Determination of Hydroxystilbene Derivative

The compound included in the peak shown by A of FIG. 1 among the reactants obtained in Example 1 was isolated by fractionation HPLC, and then dried by a usual method, whereby 110 mg of a novel compound (hereinafter referred to as UHA9021) was obtained. The UHA9021 which was isolated and purified became a brown powdery material.

Subsequently, when the molecular weight of the UHA9021 was measured using a high resolution EI-MS, the measured value was 348.3915. The following molecular formula was obtained from the comparison with the theoretical value.
Theoretical value $C_{22}H_{20}O_4(M^+)$: 348.3918
Molecular formula $C_{22}H_{20}O_4$ Next, the UHA9021 was subjected to nuclear magnetic resonance (NMR) measurement. Then, it was confirmed that the UHA9021 had the structure represented by Formula (5) from the analysis of 1H-NMR, 13C-NMR, and various two-dimensional NMR data. This shows that the hydroxystilbene derivative represented by Formula (5) can be efficiently generated by the process of the invention.

With respect to the NMR measured values, when the sites of the UHA9021 are as follows, the $^1H$ nuclear magnetic resonance spectrum and the $^{13}C$ nuclear magnetic resonance spectrum of each site are shown in Table 1.

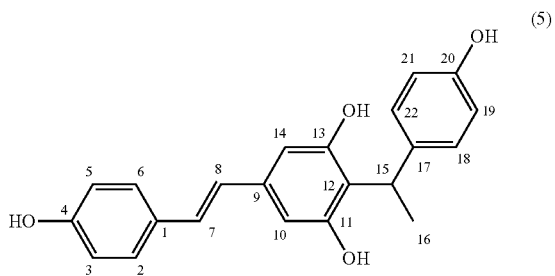 [SMILES: CC(c1ccc(O)cc1)c1c(O)cc(/C=C/c2ccc(O)cc2)cc1O]

(5)

The values are δ and ppm and are values measured with methanol-$d_3$.

TABLE 1

| | UHA9021 | |
|---|---|---|
| Site | 13C | 1H |
| 1 | 130.6 | |
| 2, 6 | 128.7 | 7.33 (2H, d, J = 8.7 Hz) |
| 3, 5 | 116.5 | 6.78 (2H, d, J = 8.7 Hz) |
| 4 | 158.0 | |
| 7 | 128.6 | 6.92 (1H, d, J = 16.5 Hz) |
| 8 | 126.7 | 6.76 (1H, d, J = 16.5 Hz) |
| 9 | 137.9 | |
| 10, 14 | 106.4 | 6.49 (2H, s) |
| 11, 13 | 157.4 | |
| 12 | 120.5 | |
| 15 | 34.2 | 4.69 (1H, d, J = 7.3 Hz) |
| 16 | 18.4 | 1.69 (1H, d, J = 7.3 Hz) |
| 17 | 138.7 | |
| 18, 22 | 129.5 | 7.22 (2H, d, J = 8.7 Hz) |
| 19, 21 | 115.4 | 6.68 (2H, d, J = 8.7 Hz) |
| 20 | 155.5 | |

The physicochemical properties of the UHA9021 were as follows.
(Property)
Brown powder
(Solubility)
Water: Poorly soluble
Methanol: Soluble
Ethanol: Soluble
DMSO: Soluble
Chloroform: Soluble
Ethyl acetate: Soluble

Example 3

Generation of Hydroxystilbene Derivative from Resveratrol and Caffeic Acid 1 g of trans-resveratrol and 1 g of caffeic acid (manufactured by Wako Pure Chemical Industries, Ltd.) were dissolved in 20 mL of ethanol, and then 20 mL of mineral water was added, thereby obtaining a solution (pH=5.1) containing resveratrol and caffeic acid. The solution containing resveratrol and caffeic acid was heated at 130° C. for 90 minutes in an autoclave. 1 mL of the obtained reactant solution was diluted with methanol in a measuring cylinder to 50 mL, and then analyzed by HPLC in the same manner as in Example 1.

Figure 2:
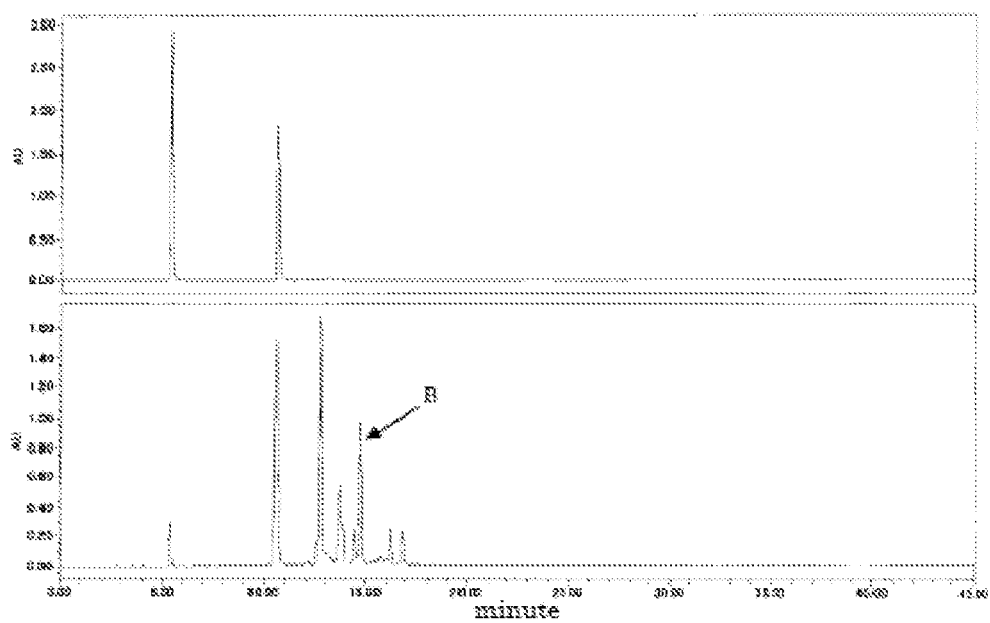
FIG. 2 show the analysis results of HPLC performed in Example 3. The upper view shows the results before a reaction and the lower view shows the results after a reaction, in which "B" represents the peak of a hydroxystilbene derivative generated using resveratrol and caffeic acid as the raw materials.

The obtained chromatograms are shown in FIG. 2. The upper view shows the chromatogram before the generation reaction and the lower view shows the chromatogram after the generation reaction. As shown in the lower view, it was confirmed that a plurality of compounds are generated including the peak B.

Example 4

Isolation and Structural Determination of Hydroxystilbene Derivative

The compound included in the peak shown by B of FIG. 2 among the reactants obtained in Example 3 was isolated by fractionation HPLC, and then dried by a usual method, whereby 80.6 mg of a novel compound (hereinafter referred to as UHA1027) was obtained. The UHA1027 which was isolated and purified became a brown powdery material.

Subsequently, when the molecular weight of the UHA1027 was measured using a high resolution EI-MS, the measured value was 364.3917. The following molecular formula was obtained from the comparison with the theoretical value.
Theoretical value C22H20O5 (M$^+$): 364.3912
Molecular formula $C_{22}H_{20}O_5$ Next, the UHA1027 was subjected to NMR measurement. Then, it was confirmed that the UHA1027 had the structure represented by Formula (6) from the analysis of 1H-NMR, $^{13}$C-NMR, and various two-dimensional NMR data. This shows that the hydroxystilbene derivative represented by Formula (6) can be efficiently generated by the process of the invention.

With respect to the NMR measured values, when the sites of the UHA1027 are as follows, the $^1$H nuclear magnetic resonance spectrum and the $^{13}$C nuclear magnetic resonance spectrum of each site are shown in Table 2.

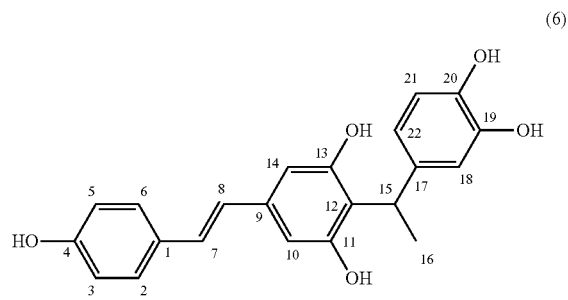 [SMILES: CC(c1ccc(O)c(O)c1)c1c(O)cc(/C=C/c2ccc(O)cc2)cc1O]

(6)

The values are δ and ppm and are values measured with methanol-d$_3$.

TABLE 2

| | UHA1027 | |
|---|---|---|
| Site | 13C | 1H |
| 1 | 130.6 | |
| 2, 6 | 128.6 | 7.33 (2H, d, J = 8.2 Hz) |
| 3, 5 | 116.4 | 6.76 (2H, m) |
| 4 | 157.9 | |
| 7 | 128.4 | 6.75 (1H, d, J = 16.0 Hz) |
| 8 | 126.9 | 6.91 (1H, d, J = 16.0 Hz) |
| 9 | 137.9 | |
| 10, 14 | 106.2 | 6.48 (2H, s) |
| 11, 13 | 157.4 | |
| 12 | 120.4 | |

TABLE 2-continued

| | UHA1027 | |
|---|---|---|
| Site | 13C | 1H |
| 15 | 34.1 | 4.64 (1H, d, J = 7.3 Hz) |
| 16 | 18.3 | 1.66 (3H, d, J = 7.3 Hz) |
| 17 | 139.4 | |
| 18 | 116.0 | 6.86 (1H, br. s) |
| 19 | 143.4 | 6.77 (1H, d, J = 8.7 Hz) |
| 20 | 145.3 | 6.75 (1H, m) |
| 21 | 115.6 | |
| 22 | 119.7 | |

The physicochemical properties of the UHA1027 were as follows.
(Property)
Brown powder
(Solubility)
Water: Poorly soluble
Methanol: Soluble
Ethanol: Soluble
DMSO: Soluble
Chloroform: Soluble
Ethyl acetate: Soluble Example 5

Generation of Hydroxystilbene Derivative from Resveratrol and Ferulic Acid 1 g of trans-resveratrol and 1 g of ferulic acid (manufactured by Wako Pure Chemical Industries, Ltd.) were dissolved in 20 mL of ethanol, and then 20 mL of mineral water was added, thereby obtaining a solution (pH=4.8) containing resveratrol and ferulic acid. The solution containing resveratrol and ferulic acid was heated at 130° C. for 90 minutes in an autoclave. 1 mL of the obtained reactant solution was diluted with methanol in a measuring cylinder to 50 mL, and then analyzed by HPLC in the same manner as in Example 1.

Figure 3:
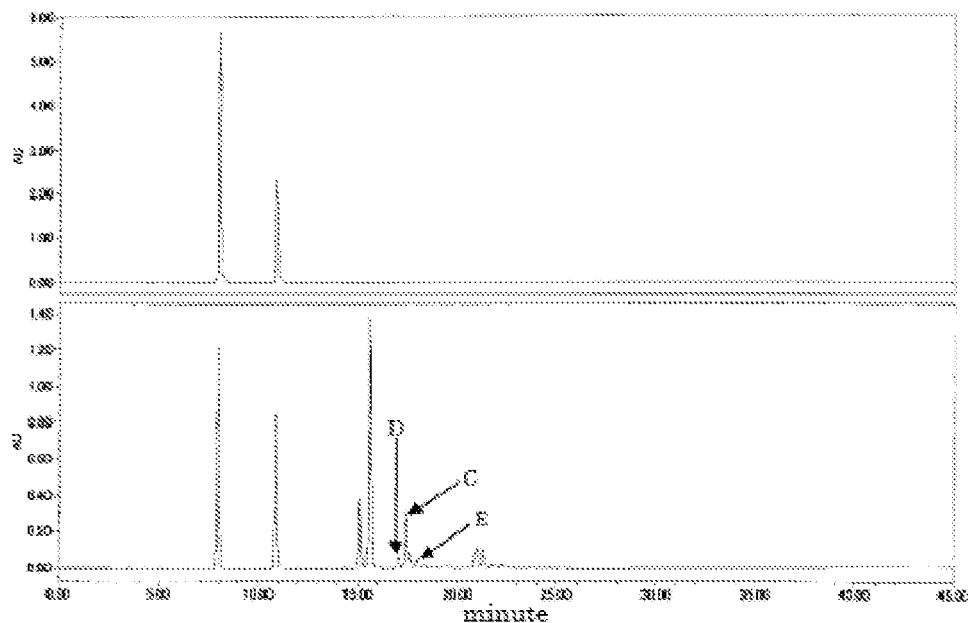
FIG. 3 show the analysis results of HPLC performed in Example 5. The upper view shows the results before a reaction and the lower view shows the results after a reaction, in which "C", "D", and "E" represent the peaks of hydroxystilbene derivatives generated using resveratrol and ferulic acid as the raw materials.

The obtained chromatograms are shown in FIG. 3. The upper view shows the chromatogram before the generation reaction and the lower view shows the chromatogram after the generation reaction. As shown in the lower view, it was confirmed that a plurality of compounds are generated including the peak C, D, and E.

Example 6

Isolation and Structural Determination of Hydroxystilbene Derivative

The compounds included in the peaks shown by C, D, and E of FIG. 3 among the reactants obtained in Example 5 were isolated by fractionation HPLC, and then dried by a usual method, whereby 120 mg of a novel brown powdery compound (hereinafter referred to as UHA1123) was obtained from the peak C, 60 mg of a novel brown powdery compound (hereinafter referred to as UHA1124) was obtained from the peak D, and 58 mg of a novel brown powdery compound (hereinafter referred to as UHA1125) was obtained from the peak E.

Subsequently, when the molecular weight of each of the UHA1123, the UHA1124, and the UHA1125 was measured using a high resolution EI-MS, the measured values each of the compounds were UHA1123: 378.4180, UHA1124:

378.4176, and UHA1125: 528.5930. The following molecular formulae were obtained from the comparison with the theoretical values.

UHA1123 and UHA1124

Theoretical value C23H22O5 (M+): 378.4178

Molecular formula $C_{23}H_{22}O_5$

UHA1125

Theoretical value C32H32O7 (M+): 598.5923

Molecular formula $C_{32}H_{32}O_7$

Next, the UHA1123, the UHA1124, and the UHA1125 were subjected to NMR measurement. Then, it was confirmed that the UHA1123 had the structure represented by Formula (7), the UHA1124 had the structure represented by Formula (8), and the UHA1125 had the structure represented by Formula (9) from the analysis of 1H-NMR, 13C-NMR, and various two-dimensional NMR data. This shows that the hydroxystilbene derivatives represented by Formulae (7) to (9) can be efficiently generated by the process of the invention.

With respect to the NMR measured values, when the sites of the UHA1123 are as follows,

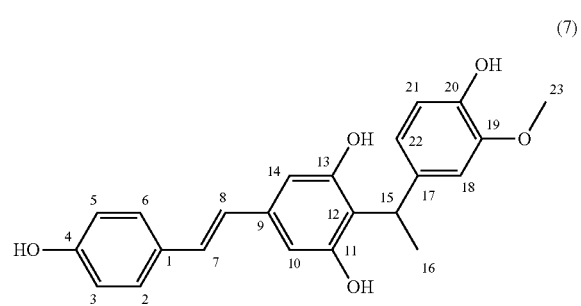 [SMILES: COc1cc(C(C)c2c(O)cc(/C=C/c3ccc(O)cc3)cc2O)ccc1O]

(7)

with respect to the NMR measured values, when the sites of the UHA1124 are as follows,

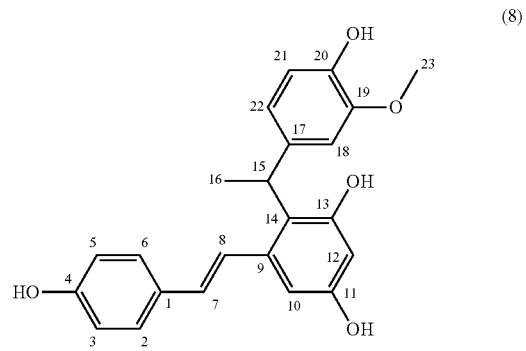 [SMILES: COc1cc(C(C)c2c(O)cc(O)cc2/C=C/c2ccc(O)cc2)ccc1O]

(8)

and with respect to the NMR measured values, when the sites of the UHA1125 are as follows,

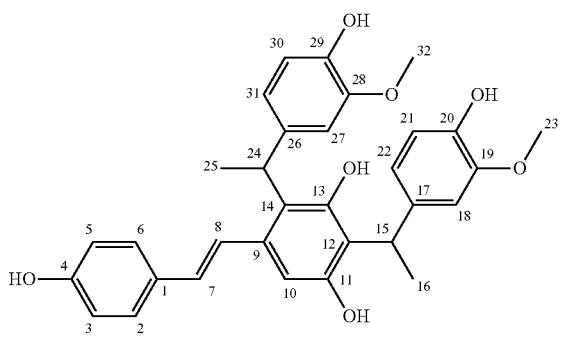

(9)

the $^1$H nuclear magnetic resonance spectrum and the $^{13}$C nuclear magnetic resonance spectrum of each site are shown in Tables 3 to 5, respectively.

The values are δ and ppm and are values measured with methanol-$d_3$.

TABLE 3

NMR data

| | UHA1123 | |
|---|---|---|
| Site | 13C | 1H |
| 1 | 130.6 | |
| 2, 6 | 128.7 | 7.32 (2H, d, J = 8.7 Hz) |
| 3, 5 | 116.5 | 6.77 (2H, d, J = 8.7 Hz) |
| 4 | 158.1 | |
| 7 | 128.6 | 6.92 (1H, d, J = 16.5 Hz) |
| 8 | 127.0 | 6.76 (1H, d, J = 16.5 Hz) |
| 9 | 138.0 | |
| 10, 14 | 106.4 | 6.48 (2H, s) |
| 11, 13 | 157.5 | |
| 12 | 120.5 | |
| 15 | 34.7 | 4.69 (1H, d, J = 7.3 Hz) |
| 16 | 18.6 | 1.69 (3H, d, J = 7.3 Hz) |
| 17 | 139.5 | |
| 18 | 112.8 | 7.00 (1H, d, J = 1.8 Hz) |
| 19 | 148.3 | |
| 20 | 144.8 | |
| 21 | 115.4 | 6.69 (1H, d, J = 7.8 Hz) |
| 22 | 121.0 | 6.85 (1H, dd, J = 1.6, 7.8 Hz) |
| 23 | 56.3 | 3.76 (3H, s) |

TABLE 4

NMR data

| | UHA1124 | |
|---|---|---|
| Site | 13C | 1H |
| 1 | 131.0 | |
| 2, 6 | 128.6 | 7.09 (2H, d, J = 8.7 Hz) |
| 3, 5 | 116.4 | 6.71 (2H, d, J = 8.7 Hz) |
| 4 | 158.0 | |
| 7 | 129.7 | 6.64 (1H, d, J = 16.0 Hz) |
| 8 | 126.8 | 6.91 (1H, d, J = 16.0 Hz) |
| 9 | 140.3 | |
| 10 | 105.8 | 6.53 (1H, d, J = 2.3 Hz) |
| 11 | 156.8 | |
| 12 | 102.9 | 6.31 (1H, d, J = 2.3 Hz) |
| 13 | 157.2 | |
| 14 | 124.4 | |
| 15 | 35.0 | 4.82 (1H, d, J = 7.3 Hz) |
| 16 | 19.5 | 1.59 (3H, d, J = 7.3 Hz) |
| 17 | 139.7 | |

TABLE 4-continued

NMR data

UHA1124

| Site | 13C | 1H |
|---|---|---|
| 18 | 112.4 | 6.84 (1H, br s) |
| 19 | 148.7 | |
| 20 | 145.0 | |
| 21 | 115.8 | 6.76 (1H, d, J = 8.2 Hz) |
| 22 | 120.5 | 6.79 (1H, br d, J = 8.2 Hz) |
| 23 | 56.3 | 3.73 (3H, s) |

TABLE 5

NMR data

UHA1125

| Site | 13C | 1H |
|---|---|---|
| 1 | 130.9 | |
| 2, 6 | 128.6 | 7.12 (2H, d, J = 8.7 Hz) |
| 3, 5 | 116.4 | 6.70 (2H, d, J = 8.7 Hz) |
| 4 | 158.0 | |
| 7 | 129.9 | 6.66 (1H, d, J = 16.0 Hz) |
| 8 | 126.4 | 6.95 (1H, d, J = 16.0 Hz) |
| 9 | 137.5 | |
| 10 | 107.1 | 6.63 (1H, s) |
| 11 | 155.0 | |
| 12 | 121.7 | |
| 13 | 154.5 | |
| 14 | 125.5 | |
| 15 | 34.6 | 4.74 (1H, d, J = 7.3) |
| 16 | 18.2 | 1.66 (1H, d, J = 7.3 Hz) |
| 17 | 138.1 | |
| 18 | 112.5 | 6.89 (1H, br. s) |
| 19 | 148.8 | |
| 20 | 145.5 | |
| 21 | 115.9 | 6.71 (1H, d, J = 8.3 Hz) |
| 22 | 120.5 | 6.83 (1H, br. d, J = 8.3 Hz) |
| 23 | 56.3 | 3.73 (3H, s) |
| 24 | 35.9 | 4.69 (1H, d, J = 7.3 Hz) |
| 25 | 19.2 | 1.56 (1H, d, J = 7.3 Hz) |
| 26 | 138.7 | |
| 27 | 112.3 | 6.74 (1H, m) |
| 28 | 148.8 | |
| 29 | 145.4 | |
| 30 | 115.8 | 6.75 (1H, m) |
| 31 | 120.3 | 6.73 (1H, m) |
| 32 | 56.3 | 3.73 (3H, s) |

The physicochemical properties of the UHA1123, the UHA1124, and the UHA1125 were all as follows.
(Property)
Brown powder
(Solubility)
Water: Poorly soluble
Methanol: Soluble
Ethanol: Soluble
DMSO: Soluble
Chloroform: Soluble
Ethyl acetate: Soluble Example 7

Generation of Hydroxystilbene Derivative from Resveratrol and Sinapic Acid 1 g of trans-resveratrol and 1 g of sinapic acid (manufactured by Wako Pure Chemical Industries, Ltd.) were dissolved in 20 mL of ethanol, and then 20 mL of mineral water was added, thereby obtaining a solution (pH=4.9) containing resveratrol and sinapic acid. The solution containing resveratrol and sinapic acid was heated at 130° C. for 90 minutes in an autoclave. 1 mL of the obtained reactant solution was diluted with methanol in a measuring cylinder to 50 mL, and then analyzed by HPLC in the same manner as in Example 1.

Figure 4:
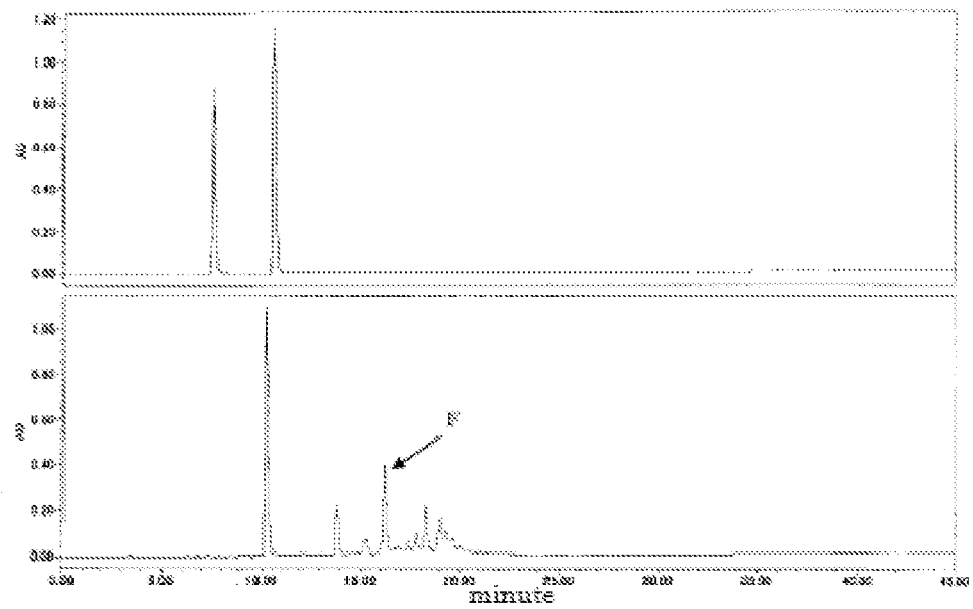
FIG. 4 show the analysis results of HPLC performed in Example 7. The upper view shows the results before a reaction and the lower view shows the results after a reaction, in which "F" represents the peak of a hydroxystilbene derivative generated using resveratrol and sinapic acid as the raw materials.

The obtained chromatograms are shown in FIG. 4. The upper view shows the chromatogram before the generation reaction and the lower view shows the chromatogram after the generation reaction. As shown in the lower view, it was confirmed that a plurality of compounds are generated including the peak F.

Example 8

Isolation and Structural Determination of Hydroxystilbene Derivative

The compound included in the peak shown by F of FIG. 4 among the reactants obtained in Example 7 was isolated by fractionation HPLC, and then dried by a usual method, whereby 129 mg of a novel compound (hereinafter referred to as UHA1028) was obtained. The UHA1028 which was isolated and purified became a brown powdery material.

Subsequently, when the molecular weight of the UHA1028 was measured using a high resolution EI-MS, the measured value was 408.4436. The following molecular formula was obtained from the comparison with the theoretical value.

Theoretical value C24H24O6 (M$^+$): 408.4438

Molecular formula $C_{24}H_{24}O_6$

Next, the UHA1028 was subjected to NMR measurement. Then, it was confirmed that the UHA1028 had the structure represented by Formula (10) from the analysis of 1H-NMR, 13C-NMR, and various two-dimensional NMR data. This shows that the hydroxystilbene derivative represented by Formula (10) can be efficiently generated by the process of the invention.

With respect to the NMR measured values, when the sites of the UHA1028 are as follows, the $^1H$ nuclear magnetic resonance spectrum and the $^{13}$nuclear magnetic resonance spectrum of each site are shown in Table 6.

(10)

The values are δ and ppm and are values measured with methanol-$d_3$.

TABLE 6

NMR data

| | UHA1028 | |
|---|---|---|
| Site | 13C | 1H |
| 1 | 130.5 | |
| 2, 6 | 128.6 | 7.32 (2H, d, J = 8.2 Hz) |
| 3, 5 | 116.4 | 6.74 (2H, d, J = 8.2 Hz) |
| 4 | 158.1 | |
| 7 | 128.5 | 6.91 (1H, d, J = 16.0 Hz) |
| 8 | 126.9 | 6.75 (1H, d, J = 16.0 Hz) |
| 9 | 138.0 | |
| 10, 14 | 106.2 | 6.48 (2H, s) |
| 11, 13 | 157.5 | |
| 12 | 120.2 | |
| 15 | 35.1 | 4.68 (1H, d, J = 7.3 Hz) |
| 16 | 18.6 | 1.69 (3H, d, J = 7.3 Hz) |
| 17 | 138.8 | |
| 18, 22 | 106.0 | 6.71 (2H, s) |
| 19, 21 | 148.5 | |
| 20 | 133.9 | |
| 23, 24 | 56.6 | 3.77 (6H, s) |

The physicochemical properties of the UHA1028 were as follows.
(Property)
Brown powder
(Solubility)
Water: Poorly soluble
Methanol: Soluble
Ethanol: Soluble
DMSO: Soluble
Chloroform: Soluble
Ethyl acetate: Soluble

Example 9

Generation of Hydroxystilbene Derivative from Pterostilbene and p-coumaric Acid 1 g of pterostilbene (manufactured by Tokyo Chemical Industry Co., Ltd.) and 1 g of p-coumaric acid were dissolved in 20 mL of ethanol, and then 20 mL of mineral water was added, thereby obtaining a solution (pH=5.0) containing pterostilbene and p-coumaric acid. The solution containing pterostilbene and p-coumaric acid was heated at 130° C. for 180 minutes in an autoclave. 1 mL of the obtained reactant solution was diluted with methanol in a measuring cylinder to 50 mL, and then analyzed by HPLC in the same manner as in Example 1.

Figure 5:
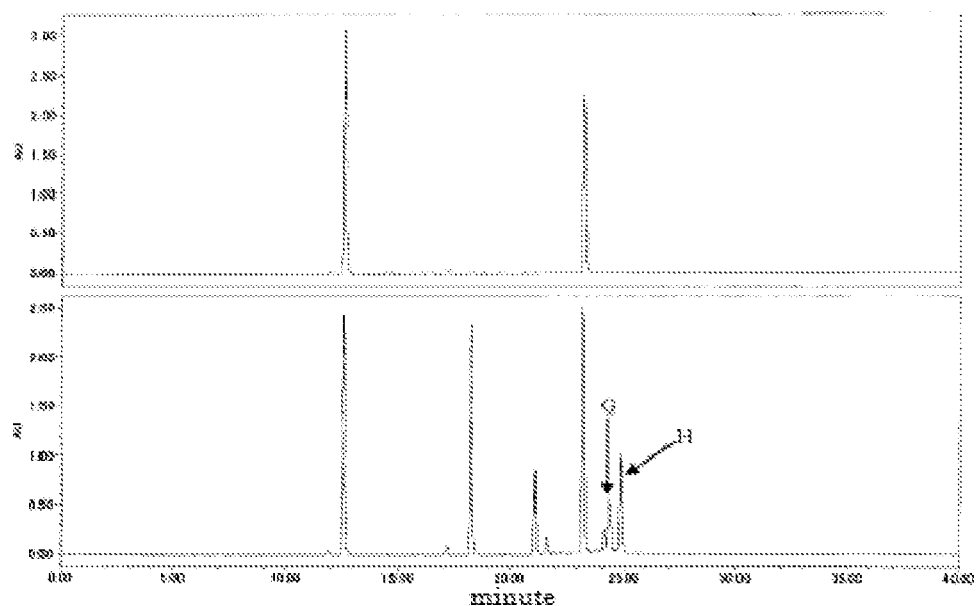
FIG. 5 show the analysis results of HPLC performed in Example 9. The upper view shows the results before a reaction and the lower view shows the results after a reaction, in which "G" and "H" represent the peaks of hydroxystilbene derivatives generated using pterostilbene and p-coumaric acid as the raw materials.

The obtained chromatograms are shown in FIG. 5. The upper view shows the chromatogram before the generation reaction and the lower view shows the chromatogram after the generation reaction. As shown in the lower view, it was confirmed that a plurality of compounds are generated including the peaks G and H.

Example 10

Isolation and Structural Determination of Hydroxystilbene Derivative

The compounds included in the peaks shown by G and H of FIG. 5 among the reactants obtained in Example 9 were isolated by fractionation HPLC, and then dried by a usual method, whereby 90 mg of a novel brown powdery compound (hereinafter referred to as UHA7032) was obtained from the peak G and 188 mg of a novel brown powdery compound (hereinafter referred to as UHA7033) was obtained from the peak H.

Subsequently, when the molecular weight of each of the UHA7032 and the UHA7033 was measured using a high resolution EI-MS, the measured values were UHA7032: 376.4452 and UHA7033: 376.4447. The following molecular formulae were obtained for both the compounds from the comparison with the theoretical values.

Theoretical value C24H24O4 (M+): 376.4450

Molecular formula $C_{24}H_{24}O_4$

Next, the UHA7032 and the UHA7033 were subjected to NMR measurement. Then, it was confirmed that the UHA7032 had the structure represented by Formula (11) and the UHA7033 had the structure represented by Formula (12) from the analysis of 1H-NMR, 13C-NMR, and various two-dimensional NMR data. This shows that the hydroxystilbene derivatives represented by Formulae (11) and (12) can be efficiently generated by the process of the invention.

With respect to the NMR measured values, when the sites of the UHA7032 are as follows,

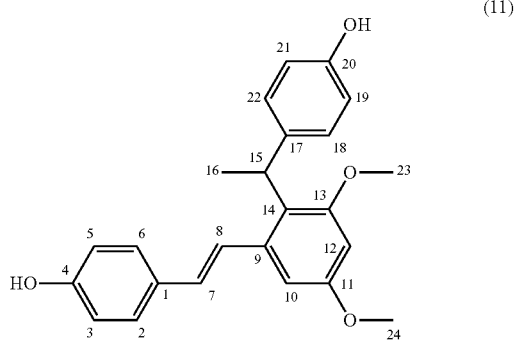 [SMILES: COc1cc(/C=C/c2ccc(O)cc2)c(C(C)c2ccc(O)cc2)c(OC)c1]
(11)

and when the sites of the UHA7033 are as follows,

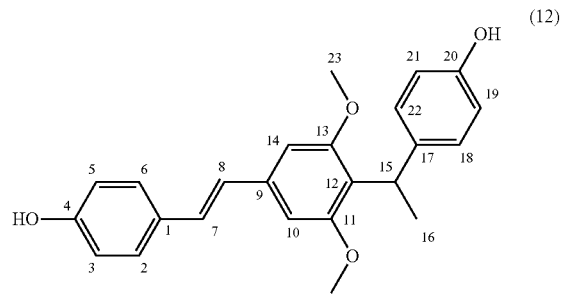
(12)

the $^1H$ nuclear magnetic resonance spectrum and the $^{13}C$ nuclear magnetic resonance spectrum of each site are shown in Tables 7 and 8, respectively.

The values are δ and ppm and are values measured with methanol-$d_3$.

TABLE 7

NMR data

| | UHA7032 | |
|---|---|---|
| Site | 13C | 1H |
| 1 | 130.1 | |
| 2, 6 | 128.7 | 7.13 (2H, d, J = 8.3 Hz) |
| 3, 5 | 116.3 | 6.73 (2H, d, J = 8.3 Hz) |
| 4 | 158.0 | |
| 7 | 130.7 | 6.72 (1H, d, J = 16.0 Hz) |
| 8 | 126.3 | 7.00 (1H, d, J = 16.0 Hz) |
| 9 | 128.8 | |
| 10 | 104.2 | 6.67 (1H, d, J = 2.3 Hz) |
| 11 | 160.1 | |
| 12 | 99.0 | 6.44 (1H, d, J = 2.3 Hz) |
| 13 | 159.9 | |
| 14 | 127.0 | |
| 15 | 34.8 | 4.79 (1H, d, J = 7.3 Hz) |
| 16 | 19.2 | 1.56 (3H, d, J = 7.3 Hz) |
| 17 | 128.4 | |
| 18, 22 | 128.7 | 7.06 (2H, d, J = 8.2 Hz) |
| 19, 21 | 115.7 | 6.72 (2H, d, J = 8.2 Hz) |
| 20 | 155.6 | |
| 23 | 56.1 | 3.61 (3H, s) |
| 24 | 55.6 | 3.77 (3H, s) |

TABLE 8

NMR data

| | UHA7033 | |
|---|---|---|
| Site | 13C | 1H |
| 1 | 130.4 | |
| 2, 6 | 128.8 | 7.33 (2H, d, J = 8.7 Hz) |
| 3, 5 | 116.4 | 6.83 (2H, d, J = 8.7 Hz) |
| 4 | 157.8 | |
| 7 | 128.8 | 6.97 (1H, d, J = 16.5 Hz) |
| 8 | 127.1 | 6.82 (1H, d, J = 16.5 Hz) |
| 9 | 138.3 | |
| 10, 14 | 103.7 | 6.62 (2H, s) |
| 11, 13 | 159.4 | |
| 12 | 123.5 | |
| 15 | 33.6 | 4.75 (1H, d, J = 7.3 Hz) |
| 16 | 18.3 | 1.62 (3H, d, J = 7.3 Hz) |
| 17 | 138.6 | |
| 18, 22 | 129.2 | 7.14 (2H, d, J = 8.7 Hz) |
| 19, 21 | 115.2 | 6.72 (2H, d, J = 8.7 Hz) |
| 20 | 155.2 | |
| 23, 24 | 56.0 | 3.60 (6H, s) |

The physicochemical properties of the UHA7032 and the UHA7033 were as follows.
(Property)
Brown powder
(Solubility)
Water: Poorly soluble
Methanol: Soluble
Ethanol: Soluble
DMSO: Soluble
Chloroform: Soluble
Ethyl acetate: Soluble

Example 11

Generation of Hydroxystilbene Derivative from Piceatannol and p-coumaric Acid 500 mg of piceatannol (manufactured by Tokyo Chemical Industry Co., Ltd.) and 500 mg of p-coumaric acid were dissolved in 10 mL of ethanol, and then 10 mL of mineral water was added, thereby obtaining a solution (pH=5.0) containing piceatannol and p-coumaric acid. The solution containing piceatannol and p-coumaric acid was heated at 130° C. for 90 minutes in an autoclave. 1 mL of the obtained reactant solution was diluted with methanol in a measuring cylinder to 50 mL, and then analyzed by HPLC in the same manner as in Example 1.

Figure 6:
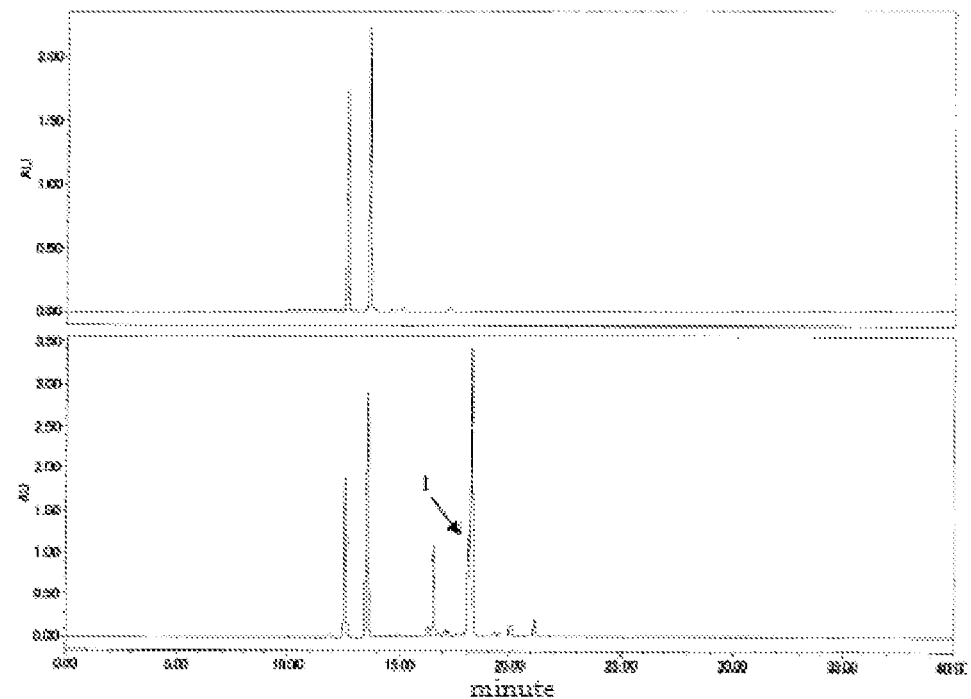
FIG. 6 show the analysis results of HPLC performed in Example 11. The upper view shows the results before a reaction and the lower view shows the results after a reaction, in which "I" represents the peak of a hydroxystilbene derivative generated using piceatannol and p-coumaric acid as the raw materials.

The obtained chromatograms are shown in FIG. 6. The upper view shows the chromatogram before the generation reaction and the lower view shows the chromatogram after the generation reaction. As shown in the lower view, it was confirmed that a plurality of compounds are generated including the peak I.

Example 12

Isolation and Structural Determination of Hydroxystilbene Derivative

The compound included in the peak shown by I of FIG. 6 among the reactants obtained in Example 11 was isolated by fractionation HPLC, and then dried by a usual method, whereby 90 mg of a novel compound (hereinafter referred to as UHA7034) was obtained. The UHA7034 which was isolated and purified became a brown powdery material.

Subsequently, when the molecular weight of the UHA7034 was measured using a high resolution EI-MS, the measured value was 364.3917. The following molecular formula was obtained from the comparison with the theoretical value.

Theoretical value C22H20O5 (M+): 364.3912

Molecular formula $C_{22}H_{20}O_5$

Next, the UHA7034 subjected to NMR measurement. Then, it was confirmed that the UHA7034 had the structure represented by Formula (13) from the analysis of 1H-NMR, 13C-NMR, and various two-dimensional NMR data. This shows that a novel piceatannol derivative represented by Formula (13) can be efficiently generated by the process of the invention.

With respect to the NMR measured values, when the sites of the UHA7034 are as follows, the $^1$H nuclear magnetic resonance spectrum and the $^{13}$C nuclear magnetic resonance spectrum of each site are shown in Table 9.

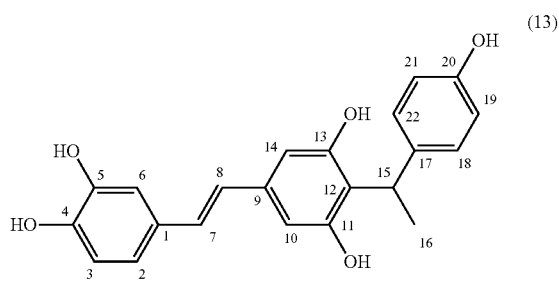 [SMILES: CC(c1ccc(O)cc1)c1c(O)cc(/C=C/c2ccc(O)c(O)c2)cc1O]

(13)

The values are δ and ppm and are values measured with methanol-$d_3$.

TABLE 9

NMR data

| | UHA7034 | |
|---|---|---|
| Site | 13C | 1H |
| 1 | 131.1 | |
| 2 | 120.0 | 6.86 (1H, d, J = 9.7 Hz) |
| 3 | 116.4 | 6.77 (1H, d, J = 9.7 Hz) |
| 4 | 146.2 | |
| 5 | 146.1 | |
| 6 | 113.7 | 7.00 (1H, s) |
| 7 | 128.7 | 6.86 (1H, d, J = 16.2 Hz) |
| 8 | 126.9 | 6.72 (1H, d, J = 16.2 Hz) |
| 9 | 137.8 | |
| 10, 14 | 106.2 | 6.48 (2H, s) |
| 11, 13 | 157.3 | |
| 12 | 120.5 | |
| 15 | 34.1 | 4.69 (1H, d, J = 7.3 Hz) |
| 16 | 18.3 | 1.69 (1H, d, J = 7.3 Hz) |
| 17 | 138.6 | |
| 18, 22 | 129.4 | 7.22 (2H, d, J = 8.7 Hz) |
| 19, 21 | 115.3 | 6.69 (2H, d, J = 8.7 Hz) |
| 20 | 155.3 | |

The physicochemical properties of the UHA7034 were as follows.
(Property)
Brown powder
(Solubility)
Water: Poorly soluble
Methanol: Soluble
Ethanol: Soluble
DMSO: Soluble
Chloroform: Soluble
Ethyl acetate: Soluble The hydroxystilbene derivatives obtained as described above, the UHA9021 represented by Formula (5), the UHA1027 represented by Formula (6), the UHA1123 represented by Formula (7), the UHA1124 represented by Formula (8), the UHA1125 represented by Formula (9), the UHA1028 represented by Formula (10), the UHA7032 represented by Formula (11), the UHA7033 represented by Formula (12), and the UHA7034 represented by Formula (13) were all investigated in a known compound database (SciFinder, Japan Association for International Chemical Information). Then, it was confirmed that the compounds are novel compounds which are not indicated in the database.

Example 13

Generation of Hydroxystilbene Derivative from Mixture of Pterostilbene or Piceatannol, and 4-hydroxycinnamic Acid Compounds (1) A mixed liquid (pH=6.0) in which 100 mg of pterostilbene and 100 mg of caffeic acid were dissolved in 2 mL of ethanol, and 2 mL of mineral water was added, (2) A mixed liquid (pH=5.9) in which 100 mg of pterostilbene and 100 mg of ferulic acid were dissolved in 2 mL of ethanol, and 2 mL of mineral water was added, (3) A mixed liquid (pH=5.7) in which 100 mg of pterostilbene and 100 mg of sinapic acid were dissolved in 2 mL of ethanol, and 2 mL of mineral water was added, (4) A mixed liquid (pH=5.9) in which 100 mg of piceatannol and 100 mg of caffeic acid were dissolved in 2 mL of ethanol, and 2 mL of mineral water was added, (5) A mixed liquid (pH=5.8) in which 100 mg of piceatannol and 100 mg of ferulic acid were dissolved in 2 mL of ethanol, and 2 mL of mineral water was added, and (6) A mixed liquid (pH=5.7) in which 100 mg of piceatannol and 100 mg of sinapic acid were dissolved in 2 mL of ethanol, and 2 mL of mineral water was added were individually prepared. Subsequently, each of the mixed liquids (1) to (6) was heated at 130° C. for 20 minutes in an autoclave. 1 mL of each of the obtained reactants was diluted as appropriate, and then the resultant reactants were subjected to LC-MS or MS measurement.

The conditions of the LC-MS/MS are as follows.

Column: Negative-phase column "Develosil (Registered Trademark) C-30-UG-5" (2.0 mmi.d.×150 mm)

Mobile phase: A—$H_2O$ (0.1% formic acid), B—Acetonitrile (0.1% formic acid)

Flow velocity: 0.2 mL/min

Pouring: 10 µL

Detection: 3200QTRAP (Registered Trademark) LC-MS/MS system (manufactured by AB SCIEX)

Gradient (% by capacity): From 100% A/0% B to 0% A/80% B for 33 minutes and 100% B for 7 minutes (all straight line)

As a result, the molecular weight was confirmed by [M-H] in the Negative mode. As the value of the major peak which was considered to show a hydroxystilbene derivative.

(1) 391(a), 391(b), 527, (2) 405(a), 405(b), 555, (3) 435(a), 435(b), 615

(4) 379(a), 379(b), 515, (5) 393(a), 393(b), 543

(6) 423(a), 423(b), and 603 were confirmed.

The isolation and the structural determination for the hydroxystilbene derivatives contained in the peaks were not performed. However, from the results of Examples 1 to 12, it is expected that hydroxystilbene derivatives represented by the following formulae were generated.

Hydroxystilbene derivative of a molecular weight of 391(a) of (1):

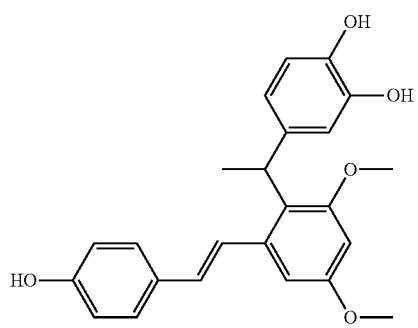 [SMILES: COc1cc(/C=C/c2ccc(O)cc2)c(C(C)c2ccc(O)c(O)c2)c(OC)c1]

Hydroxystilbene derivative of a molecular weight of 391(b) of (1):

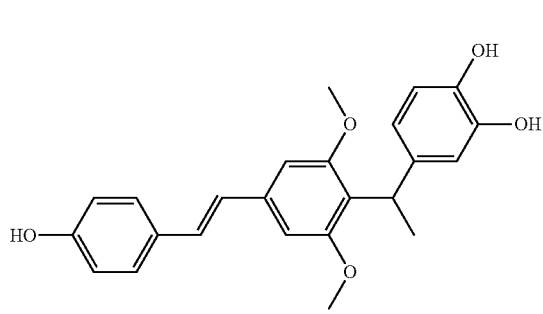 [SMILES: COc1cc(/C=C/c2ccc(O)cc2)cc(OC)c1C(C)c1ccc(O)c(O)c1]

Hydroxystilbene derivative of a molecular weight of 527 of (1):

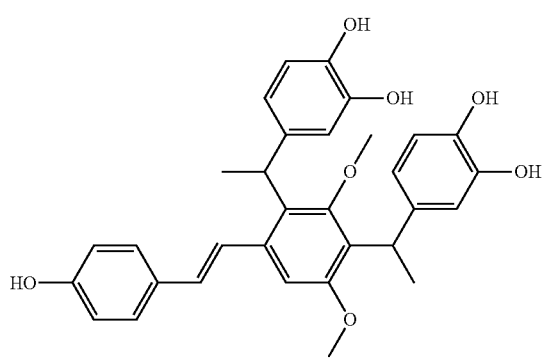 [SMILES: COc1cc(/C=C/c2ccc(O)cc2)c(C(C)c2ccc(O)c(O)c2)c(OC)c1C(C)c1ccc(O)c(O)c1]

Hydroxystilbene derivative of a molecular weight of 405(a) of (2):

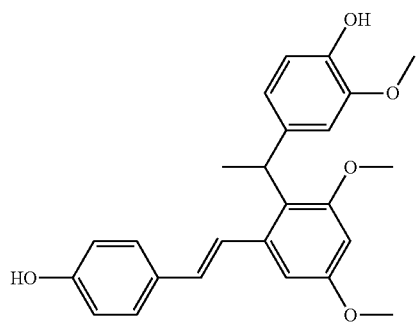 [SMILES: COc1cc(/C=C/c2ccc(O)cc2)c(C(C)c2ccc(O)c(OC)c2)c(OC)c1]

Hydroxystilbene derivative of a molecular weight of 405(b) of (2):

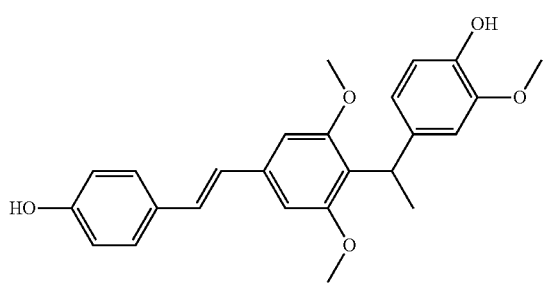 [SMILES: COc1cc(C(C)c2c(OC)cc(/C=C/c3ccc(O)cc3)cc2OC)ccc1O]

Hydroxystilbene derivative of a molecular weight of 555 of (2):

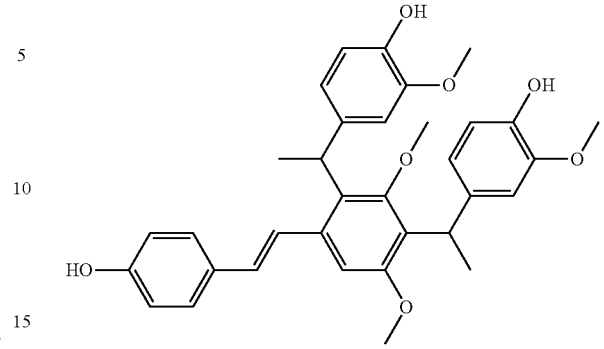

Hydroxystilbene derivative of a molecular weight of 435(a) of (3):

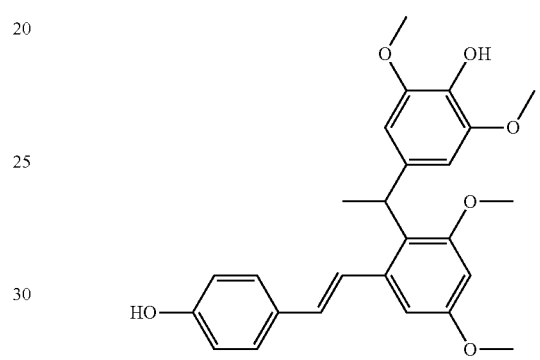

Hydroxystilbene derivative of a molecular weight of 435(b) of (3):

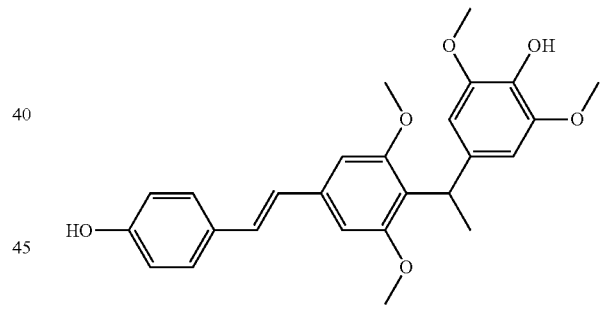

Hydroxystilbene derivative of a molecular weight of 615 of (3):

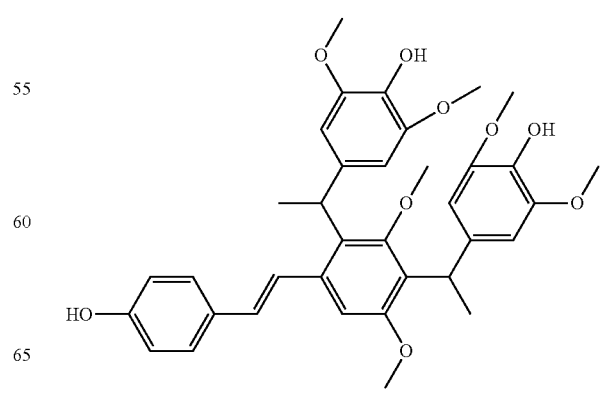

Hydroxystilbene derivative of a molecular weight of 379(a) of (4):

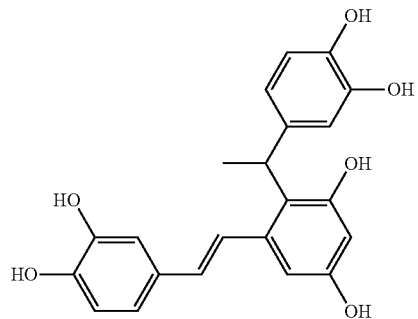 [SMILES: CC(c1ccc(O)c(O)c1)c1c(O)cc(O)cc1/C=C/c1ccc(O)c(O)c1]

Hydroxystilbene derivative of a molecular weight of 379(b) of (4):

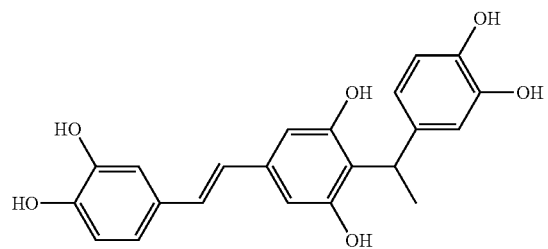 [SMILES: CC(c1ccc(O)c(O)c1)c1c(O)cc(/C=C/c2ccc(O)c(O)c2)cc1O]

Hydroxystilbene derivative of a molecular weight of 515 of (4):

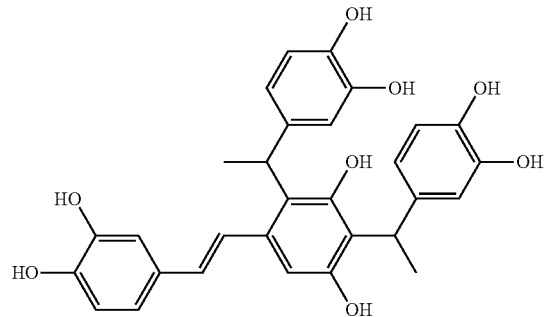 [SMILES: CC(c1ccc(O)c(O)c1)c1c(O)cc(/C=C/c2ccc(O)c(O)c2)c(C(C)c2ccc(O)c(O)c2)c1O]

Hydroxystilbene derivative of a molecular weight of 393(a) of (5):

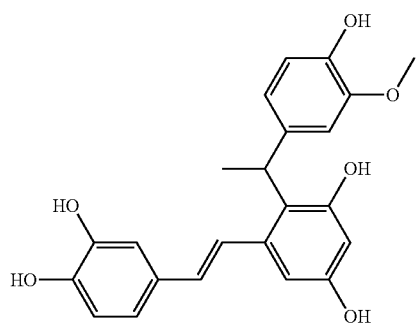 [SMILES: COc1cc(C(C)c2c(O)cc(O)cc2/C=C/c2ccc(O)c(O)c2)ccc1O]

Hydroxystilbene derivative of a molecular weight of 393(b) of (5):

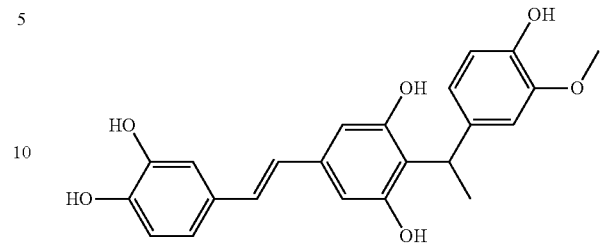

Hydroxystilbene derivative of a molecular weight of 543 of (5):

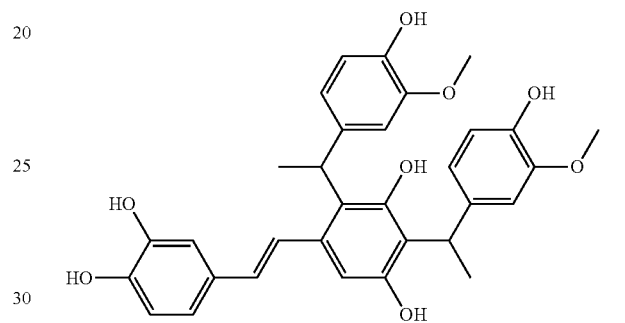

Hydroxystilbene derivative of a molecular weight of 423(a) of (6):

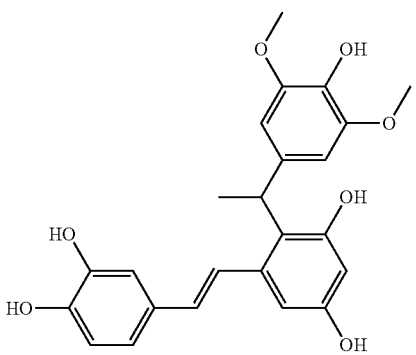 [SMILES: COc1cc(C(C)c2c(O)cc(O)cc2/C=C/c2ccc(O)c(O)c2)cc(OC)c1O]

Hydroxystilbene derivative of a molecular weight of 423(b) of (6):

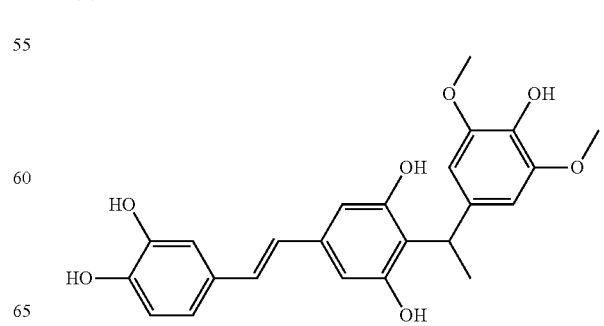

Hydroxystilbene derivative of a molecular weight of 603 of (6):

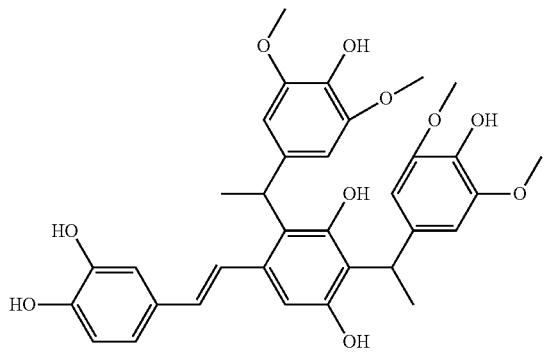 [SMILES: COc1cc(C(C)c2c(O)cc(/C=C/c3ccc(O)c(O)c3)c(C(C)c3cc(OC)c(O)c(OC)c3)c2O)cc(OC)c1O]

Example 14

Generation of Hydroxystilbene Derivative from Mixture of Two or More Kinds of Hydroxystilbenes and Two or More Kinds of 4-hydroxycinnamic Acid Compounds In order to examine the reaction from two or more kinds of hydroxystilbenes and two or more kinds of 4-hydroxycinnamic acid compounds, a mixed liquid (pH=5.5) obtained by mixing 100 mg of p-coumaric acid, 100 mg of ferulic acid, 100 mg of resveratrol, and 100 mg of pterostilbene, dissolving the mixture in 2 mL of ethanol, and then adding 2 mL of mineral water was heated at 130° C. for 40 minutes in an autoclave. 1 mL of the obtained reactant was diluted with methanol in a measuring cylinder to 50 mL. Then, 10 μL of the resultant reactant was subjected to the same LC-MS/MS under the same conditions as those of Example 13.

As a result, even in the case of three or more kinds of substances, the molecular weight (405(a), 405(b), and 555) of each of the UHA9021, the UHA1123, the UHA1124, the UHA1125, the UHA7032, the UHA7033, and Example 13(2) was confirmed and it was also confirmed that the hydroxystilbene derivative was generated even from the mixture of the two or more kinds of hydroxystilbenes and the two or more kinds of 4-hydroxycinnamic acid compounds.

From the results of Examples 13 and 14, it was confirmed that, even in the case of the reaction of the mixed liquid of various kinds of compounds, the reaction proceeded. This shows that the application and the use thereof to a random library can be expected.

Example 15

Anti-cancer Action of Hydroxystilbene Derivative

Next, in order to see the effect of the hydroxystilbene derivative to cancer cells, cancer cell growth suppressing action using HL-60 cells (human promyelocytic leokemia cells) was tested.

For culturing the HL-60 cells, an enriched culture medium "RPMI-1640" (manufactured by Sigma-Aldrich Japan) containing 4 mM glutamine (L-Glutamine, manufactured by Sigma-Aldrich Japan) and 10% FBS (Foetal Bovine Serum, manufactured by Biological Industries) was used. For the test, a 96-well plate for cell culture (manufactured by Corning Japan) was used, and the HL-60 cells whose number of cells was adjusted to be 5×10⁵ cells/mL were seeded at 100 μL per well As samples, p-coumaric acid, ferulic acid, caffeic acid, sinapic acid, resveratrol, pterostilbene, and the UHA1027, the UHA1028, the UHA1123, the UHA1124, the UHA1125, the UHA7032, the UHA7033, and the UHA9021 which were already purified were used. With respect to the preparation of the samples, each compound was dissolved in DMSO (Wako Pure Chemical Industries, Ltd.), and then adjusted in such a manner that the final concentration in the HL-60 cell culture solutions was 6.3 μM, 12.5 μM, 25 μM, 50 μM, and 100 μM. Then, the test was started.

The number of viable cells was quantified by an MTT method using a "Cell counting kit-8" (manufactured by DOJINDO LABORATORIES). 24 hours after starting the test, 10 μL of a Cell counting kit-8 solution was added to each well, and then sufficiently stirred. After a shading reaction for 1 hour, the absorbancy was measured at a measurement wavelength of 450 nm using a plate leader (Biorad Laboratories, Inc., "BIO-RAD Model 680"). Then, the cell viability was calculated based on the obtained data. The cell viability is a value obtained by setting the number of viable cells of the culture liquid to which only DMSO as a solvent was added to 100%, and then calculating the number of viable cells under the concentration of each compound as a relative value. From the relationship between the concentration of each compound and the cell viability, the concentration $IC_{50}$ (50% inhibition concentration) at which the cell growth is suppressed by 50% was calculated. The results are shown in Table 10. From these results, a cancer cell growth suppressing ability higher than that of the 4-hydroxycinnamic acid compounds and the hydroxystilbenes which are the raw materials was observed in each of the hydroxystilbene derivatives.

TABLE 10

| | Cell growth suppressing ability to HL-60 (IC50, μM) |
|---|---|
| p-coumaric acid | >100 |
| Coffeic acid | >100 |
| Ferulic acid | >100 |
| Sinapic acid | >100 |
| Resveratrol | 76.5 |
| UHA9021 | 43.4 |
| UHA1123 | 31.5 |
| UHA1124 | 14.4 |
| UHA1125 | 13.4 |
| UHA1027 | 5.9 |
| UHA1028 | 14.1 |
| Pterostilbene | 60.4 |
| UHA7032 | 31.0 |
| UHA7033 | 35.5 |

Example 16

Anti-cancer Action to Oral Cancer of Hydroxystilbene Derivative

Next, in order to see the effect of the hydroxystilbene derivative to oral cancer cells, cancer cell growth suppressing action using SCC-4 cells (human oral cancer cells, ATCC) was tested.

For culturing the SCC-4 cells, a DMEM/F-12 (1:1) culture medium (manufactured by GIBCO) containing 400 ng/mL hydrocortisone (manufactured by Sigma-Aldrich Japan), 1% antibiotic-antimycotic (manufactured by GIBCO), and 10% FBS (Foetal Bovine Serum, manufactured by ATCC) was used. For the test, a collagen I coat 96 well plate for cell culture (manufactured by Japan BD) was used, and SCC-4 cells whose number of cells was adjusted to be 5×10⁵ cells/mL were seeded at 100 μL per well. The cells were cultured under the conditions of 37° C. and 5% $CO_2$ for 24 hours, and were used for the test in a confluent state of 80% or higher.

As samples, p-coumaric acid, ferulic acid, caffeic acid, sinapic acid, resveratrol, pterostilbene, piceatannol, and the UHA1027, the UHA1028, the UHA1123, the UHA1124, the UHA1125, the UHA7032, the UHA7033, the UHA7034, and the UHA9021 which were already purified were used. With respect to the preparation of the samples, each compound was dissolved in DMSO, and then prepared in such a manner as to achieve 0.63 mM, 1.25 mM, 2.5 mM, 5 mM, and 10 mM. The samples were added in such a manner that the final concentration in the SCC-4 cell culture solution was 6.3 μM, 12.5 μM, 25 μM, 50 μM, and 100 μM. Then, the test was started. A sample to which an equivalent amount of only DMSO as the solvent was added was used as a negative control.

The number of viable cells was quantified by an MTT method using a "Cell counting kit-8" in the same manner as in Example 15, and the concentration $IC_{50}$ at which the cell growth is suppressed by 50% was calculated. The results are shown in Table 11. From these results, a cancer cell growth suppressing ability higher than that of the 4-hydroxycinnamic acid compounds and the hydroxystilbenes which are the raw materials was observed in each of the hydroxystilbene derivatives.

TABLE 11

| Compound | Cell growth suppressing ability ($IC_{50}$, μM) |
| --- | --- |
| p-coumaric acid | >100 |
| Coffeic acid | >100 |
| Ferulic acid | >100 |
| Sinapic acid | >100 |
| Resveratrol | >100 |
| UHA9021 | 38.2 |
| UHA1123 | 50.3 |
| UHA1124 | 17.4 |
| UHA1125 | 26.1 |
| UHA1027 | 28.9 |
| UHA1028 | 17.6 |
| Pterostilbene | 73.9 |
| UHA7032 | 37.0 |
| UHA7033 | 41.7 |
| Piceatannol | >100 |
| UHA7034 | 49.6 |

Example 17

Lipase Inhibitory Action of Hydroxystilbene Derivative

In order to see the inhibitory action to lipase of the hydroxystilbene derivative, an inhibitory action test using rat intestine derived lipase was performed.

As lipase, one obtained by suspending 100 mg of rat derived intestine acetone powder (manufactured by Sigma-Aldrich Japan) in 1 mL of 100 mM citric acid buffer (pH 6.0), stirred at 4° C. for 1 hour, centrifuging the same (at 15000 rpm for 45 minutes at 4° C.), and then diluting the supernatant by 1500 times was used as a lipase solution.

As samples, p-coumaric acid, caffeic acid, sinapic acid, resveratrol, and the UHA1027, the UHA1028, and the UHA9021 which were already purified were used. With respect to the preparation of the samples, each compound was dissolved in DMSO, and then prepared in such a manner as to achieve 0.1 mM, 0.5 mM, 1 mM, 2 mM, and 4 mM.

For measuring the activity, a "Lipase kit S" (Trade name, manufactured by Dainippon Pharmaceutical Co., Ltd.) was used. First, in accordance with a preparation method described in the catalog of the Lipase kit S, a color developing liquid was prepared. Reaction liquids in which 70 μl of the color developing liquid, 2 μl of an esterase inhibitor, 10 μl of the lipase solution, and 10 μl of the samples (Final concentration: 10 μM, 50 μM, 100 μM, 200 μM, 400 μM, and 1000 μM) were mixed were prepared, preincubated at 30° C. for 5 minutes, and then 8 μl of a substrate solution described in the catalog was added. Then, a reaction was started. After reacting for 10 minutes, 150 μl of a reaction stop liquid prepared in accordance with the preparation method described in the catalog of the Lipase kit S was added to stop the reaction. The resultant substance was subjected to a measurement of absorbancy at a wavelength of 415 nm. A reaction liquid to which only DMSO as the solvent of the sample was added was used as a positive control and one to which 10 μl of 100 mM citric acid buffer (pH 6.0) was added instead of the lipase solution was used as a negative control. From the relationship between the lipase inhibition rate calculated based on the data obtained therefrom and the concentration of each compound, the concentration $IC_{50}$ at which the lipase activity is inhibited by 50% was calculated. The results are shown in Table 12.

TABLE 12

| | Lipase inhibitory action (IC50, μM) |
| --- | --- |
| p-coumaric acid | >1000 |
| Coffeic acid | >1000 |
| Sinapic acid | >1000 |
| Resveratrol | >1000 |
| UHA9021 | 330.7 |
| UHA1027 | 451.8 |
| UHA1028 | 509.5 |

From these results, a lipase inhibition activity higher than that of the raw materials was observed in the hydroxystilbene derivatives. Accordingly, since the hydroxystilbene derivatives demonstrate outstanding lipase inhibitory action, it is considered that the compounds are useful as anti-obesity agents and also as metabolic syndrome prevention agents. Since the lipase inhibition on the skin is effective for prevention of pimples and recovery from pimples, it is considered that the compounds are useful also as skin disease therapeutic agents for prevention of pimples, recovery of pimples, and the like.

Hereinafter, compounding examples of the hydroxystilbene derivative represented by Formula (5) obtained using resveratrol and p-coumaric acid as the raw materials is described as Examples of extracts containing the hydroxystilbene derivative, foods containing the extracts containing the hydroxystilbene derivative, pharmaceutical agents containing the hydroxystilbene derivative, quasi-drugs containing hydroxystilbene derivative, and cosmetics containing the hydroxystilbene derivative but it is a matter of course that other hydroxystilbene derivatives can be similarly used.

As substances containing the 4-hydroxycinnamic acid compound serving as the raw materials, propolis extracts and the like may be used as p-coumaric acid and artepillin C, coffee and SHIMON tea (dried product of sweet potato leaf portion) and enzyme-treated substances thereof may be used as caffeic acid, ferulic acid and rice bran extracts of food additives may be used as ferulic acid, and extracts of mustard, Japanese horseradish, and the like, enzyme-treated substances thereof, and the like, may be used as sinapic acid but the substances containing the 4-hydroxycinnamic acid compound are not limited thereto. With respect to the substances containing the hydroxystilbenes, extracts of fruits and seeds of grapes and the skin of peanuts may be used as resveratrol, extracts of fruits and seeds of grapes, fruits of berries, and the like may be used as pterostilbene, and piceatannol but the substances are not limited thereto.

Example 18

Preparation of Extracts Containing UHA9021

A mixed solution prepared by adding 10 g of powder of grape pericarp extract (resveratrol raw material), 10 g of propolis extract (p-coumaric acid raw material), 10 mL of ethanol, and 10 mL of mineral water was heated at 130° C. for 60 minutes in an autoclave. The obtained reaction solution was heated under reduced pressure to dry the same for solidification, thereby obtaining 13 g of an extract containing UHA9021. In 13 g of the UHA9021 extract thus obtained, 0.095 g of the UHA9021 was contained as confirmed by the same technique as that of Example 1. The operation was repeated as required.

Example 19

Food Containing UHA9021

1 g of the extract containing UHA9021 obtained in Example 18 was dissolved in 100 mL of ethanol beforehand, 500 g of sugar and 400 g of starch syrup were mixed and dissolved in the solution, and then 100 g of fresh cream, 20 g of butter, 70 g of condensed milk, and 1.0 g of emulsifier were mixed in the mixture. Then, the pressure was reduced to -550 mmHg in a vacuum pan, and then the resultant mixture was condensed under the conditions of 115° C., thereby obtaining a milk hard candy having a moisture value of 3.0% by weight. It is a matter of course that the milk hard candy is easy to eat as a confectionery. Moreover, the milk hard candy can be used also as a functional food which is expected to improve obesity, to prevent obesity, to reduce the risk of diffusion of cancer in cancer patients, to reduce the risk of the onset of cancer, and to prevent cancer.

Example 20

Pharmaceutical Agent Containing UHA9021

The UHA9021 obtained by the same process as that of Example 2 was dissolved in ethanol, adsorbed to microcrystalline cellulose, and then dried under reduced pressure. The resultant substance was treated according to a usual method, thereby obtaining a tablet product. The formula is as follows: 10 parts by weight of UHA9021, 23 parts by weight of cornstarch, 12 parts by weight of milk sugar, 8 parts by weight of carboxymethyl cellulose, 32 parts by weight of microcrystalline cellulose, 4 parts by weight of polyvinyl pyrrolidone, 3 parts by weight of magnesium stearate, and 8 parts by weight of talc. The tablet product can be effectively used as a pharmaceutical agent aiming at curing cancer.

Example 21

Quasi-drug Containing UHA9021

1.2 g of the UHA9021 obtained by the process of Example 2 was dissolved in 10 mL of ethanol, 20 g of taurine, 0.12 g of vitamin B1 nitrate, 0.6 g of sodium benzoate, 4 g of citric acid, 60 g of sugar, and 10 g of polyvinyl pyrrolidone were all dissolved in purified water, and then the solution was diluted in a measuring cylinder to 1000 mL. The pH of the obtained solution was adjusted to 3.2 using dilute hydrochloric acid. 50 mL of 1000 mL of the obtained solution was charged into a glass bottle, and then sterilized at 80° C. for 30 minutes, thereby completing a think agent which is a quasi-drug. Since the drink agent contains the UHA9021, the drink agent can be effectively used as a quasi-drug aiming at improvement of obesity, prevention of obesity, reduction of the risk of diffusion of cancer in cancer patients, reduction of the risk of the onset of cancer, and prevention of cancer in addition to the purpose of supply of nutrients.

Example 22

Cosmetics Containing UHA9021

1 part by weight of tetraoleic acid polyoxyethylene sorbitol, 0.5 part by weight of polyoxyethylene stearyl ether, 1 part by weight of lipophilic glyceryl monostearate, 0.5 part by weight of pyruvic acid, 0.5 part by weight of stearyl alcohol, 1 part by weight of avocado oil, and 0.1 part by weight of powder of the UHA9021 obtained by the same process as that of Examples 1 and 2 were mixed, the mixture was dissolved according to a usual method, 1 part by weight of sodium lactate, 5 parts by weight of propylene glycol, 0.1 part by weight of carboxy vinyl polymer, a very slight amount of spice, and 89.3 parts by weight of purified water were added thereto, and the mixture was treated by a homogenizer for emulsification, thereby obtaining a milky lotion. Since the milky lotion contains the UHA9021, the milky lotion can be effectively used as medicated cosmetics having medical treatment and prevention effects of skin diseases, such as pimples.

The invention claimed is:
1. A process for producing a hydroxystilbene derivative represented by Formula (1):

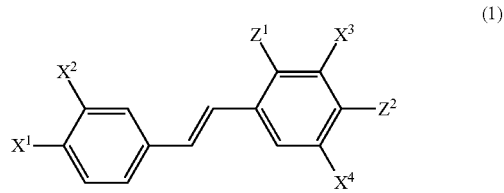

wherein, in Formula (1), $X^1$-$X^4$ represent a hydrogen atom, a hydroxy group, a saturated or unsaturated linear or branched alkoxy group having 1-10 carbon atoms, or a saturated or unsaturated linear or branched alkyl group having 1-10 carbon atoms;
$Z^1$ and $Z^2$ represent a hydrogen atom or a group represented by Formula (2):

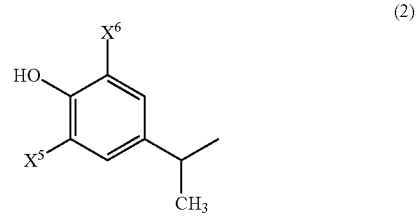

wherein, in Formula (2), $X^5$ and $X^6$ represent a hydrogen atom, a hydroxy group, a saturated or unsaturated linear or branched alkoxy group having 1-10 carbon atoms, or a saturated or unsaturated linear or branched alkyl group having 1-10 carbon atoms; and
$Z^1$ and $Z^2$ may be the same or different from each other;
wherein $X^1$-$X^6$ may be the same or different from one another,
the process comprising heating 4-hydroxycinnamic acid compounds and hydroxystilbenes in the presence of a metal salt.

2. The process according to claim 1, wherein the 4-hydroxycinnamic acid compounds are represented by the following formula (3):

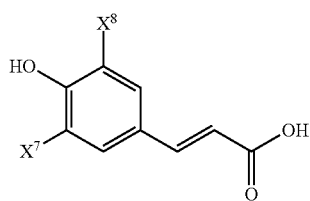

(3)

wherein $X^7$ and $X^8$ represent a hydrogen atom, a hydroxy group, a saturated or unsaturated linear or branched alkoxy group having 1-10 carbon atoms, or a saturated or unsaturated linear or branched alkyl group having 1-10 carbon atoms, and $X^7$ and $X^8$ may be the same or different from each other.

3. The process according to claim 2, wherein the 4-hydroxycinnamic acid compounds are at least one compound selected from the group consisting of p-coumaric acid, ferulic acid, caffeic acid, sinapic acid, di-t-butyl hydroxycinnamic acid compound, and artepillin C.

4. The process according to claim 1, wherein the hydroxystilbenes are represented by the following formula (4):

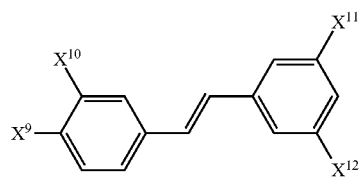

(4)

wherein $X^9$-$X^{12}$ represent a hydrogen atom, a hydroxy group, a saturated or unsaturated linear or branched alkoxy group having 1-10 carbon atoms, or a saturated or unsaturated linear or branched alkyl group having 1-10 carbon atoms, and $X^9$-$X^{12}$ may be the same or different from one another.

5. The process according to claim 4, wherein the hydroxystilbenes are at least one compound selected from the group consisting of resveratrol, piceatannol, and pterostilbene.

6. The process according to claim 1, wherein the 4-hydroxycinnamic acid compounds are at least one compound selected from the group consisting of p-coumaric acid, ferulic acid, caffeic acid, sinapic acid, di-t-butyl hydroxycinnamic acid compound, and artepillin C, and the hydroxystilbenes are one or more kinds of compounds selected from the group consisting of resveratrol, piceatannol, and pterostilbene.

7. The process according to claim 6, wherein the hydroxystilbene derivative generated by heating p-coumaric acid and resveratrol in the presence of the metal salt is a compound represented by Formula (5):

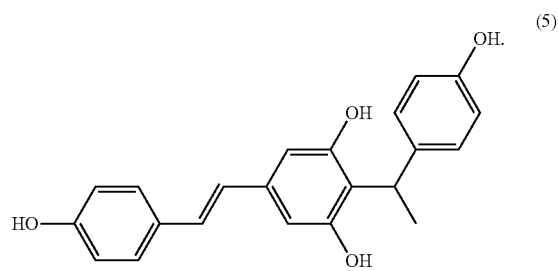 [SMILES: CC(c1ccc(O)cc1)c1c(O)cc(/C=C/c2ccc(O)cc2)cc1O]

(5)

8. The process according to claim 6, wherein the hydroxystilbene derivative generated by heating caffeic acid and resveratrol in the presence of the metal salt is a compound represented by Formula (6):

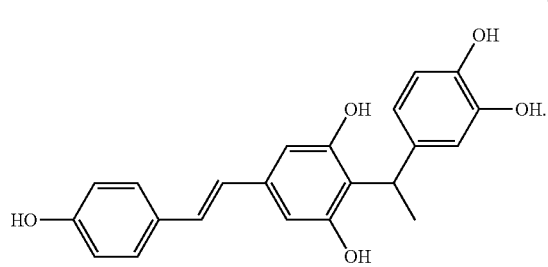

(6)

9. The process according to claim 6, wherein the hydroxystilbene derivative generated by heating ferulic acid and resveratrol in the presence of the metal salt is a compound represented by Formula (7):

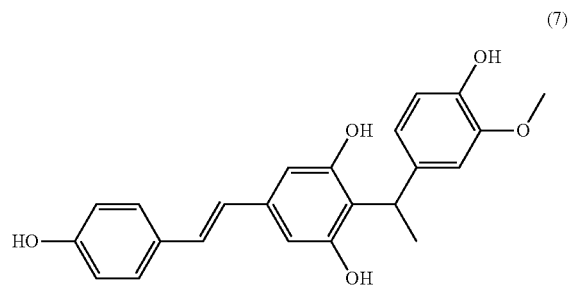 [SMILES: CC(c1ccc(O)c(O)c1)c1c(O)cc(/C=C/c2ccc(O)cc2)cc1O]

(7)

Formula (8):

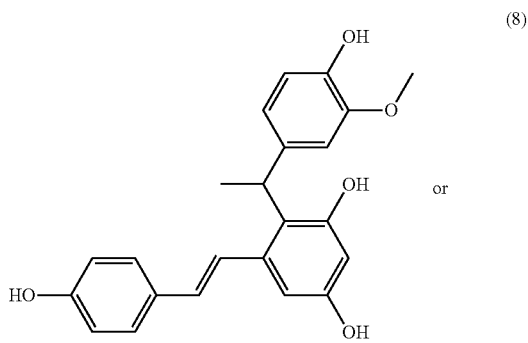

(8)

or

Formula (9):

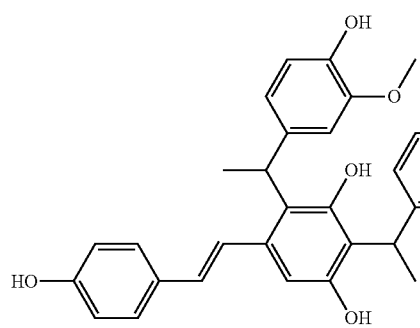

(9)

10. The process according to claim 6, wherein the hydroxystilbene derivative generated by heating sinapic acid and resveratrol in the presence of the metal salt is a compound represented by Formula (10):

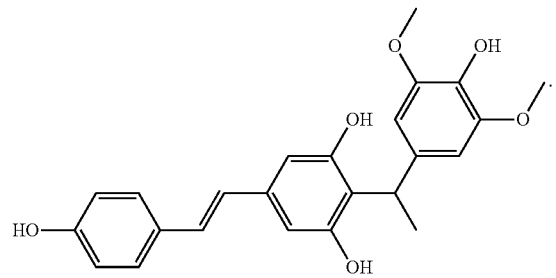

(10)

11. The process according to claim 6, wherein the hydroxystilbene derivative generated by heating p-coumaric acid and pterostilbene in the presence of the metal salt is a compound represented by Formula (11):

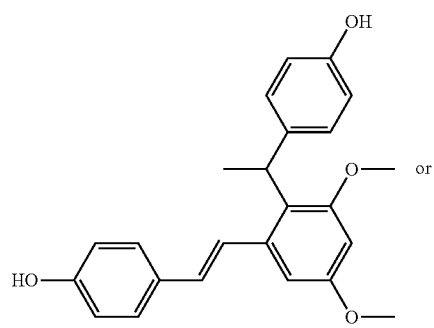

(11)

Formula (12):

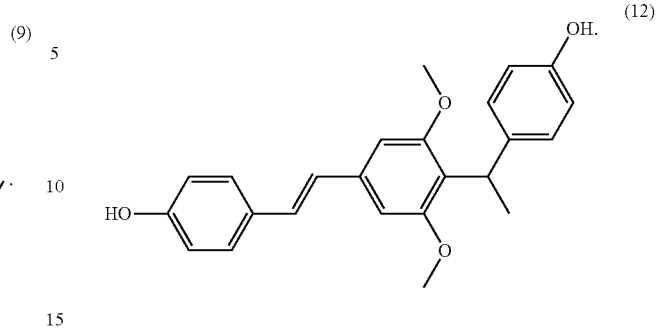

(12)

12. The process according to claim 6, wherein the hydroxystilbene derivative generated by heating p-coumaric acid and piceatannol in the presence of the metal salt is a compound represented by Formula (13):

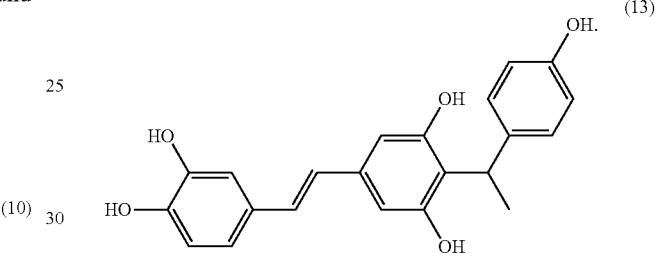

(13)

13. The process according to claim 1, comprising performing heat treatment at 90° C. to 150° C.

14. A novel hydroxystilbene derivative represented by Formula (5) or a pharmacologically permissible salt thereof:

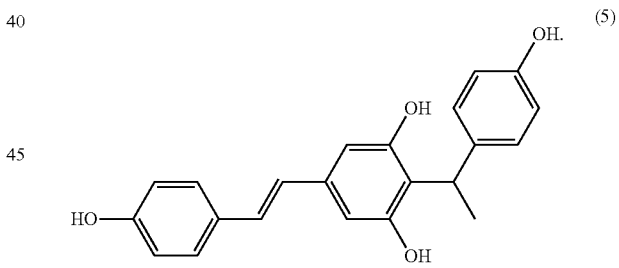

(5)

15. A novel hydroxystilbene derivative represented by Formula (6) or a pharmacologically permissible salt thereof:

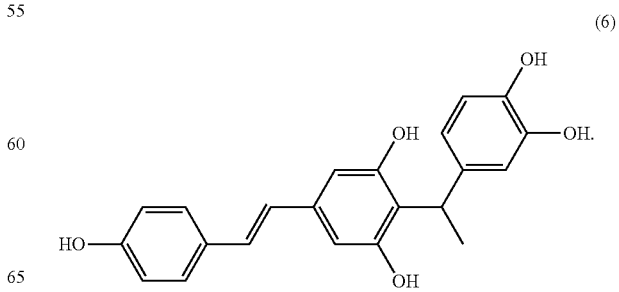

(6)

16. A novel hydroxystilbene derivative represented by Formula (7) or a pharmacologically permissible salt thereof:

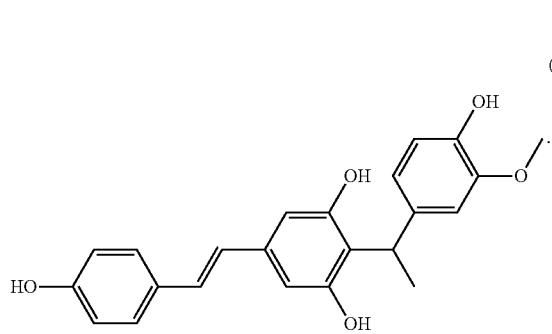
(7)

17. A novel hydroxystilbene derivative represented by Formula (8) or a pharmacologically permissible salt thereof:

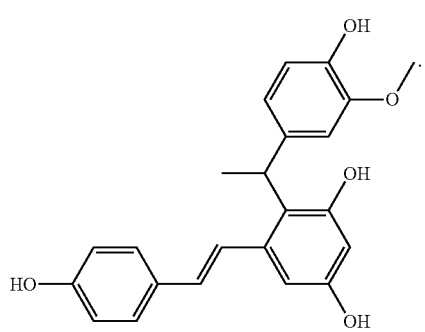
(8)

18. A hydroxystilbene derivative represented by Formula (9) or a pharmacologically permissible salt thereof:

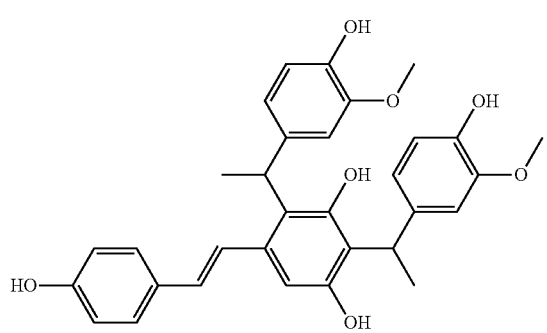
(9)

19. A novel hydroxystilbene derivative represented by Formula (10) or a pharmacologically permissible salt thereof:

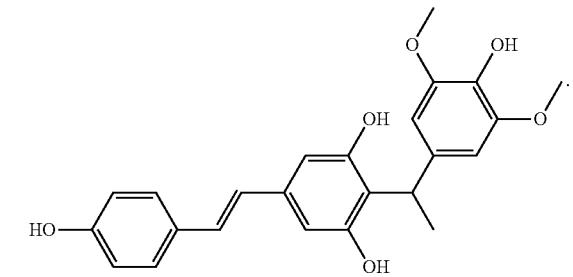
(10)

20. A novel hydroxystilbene derivative represented by Formula (11) or a pharmacologically permissible salt thereof:

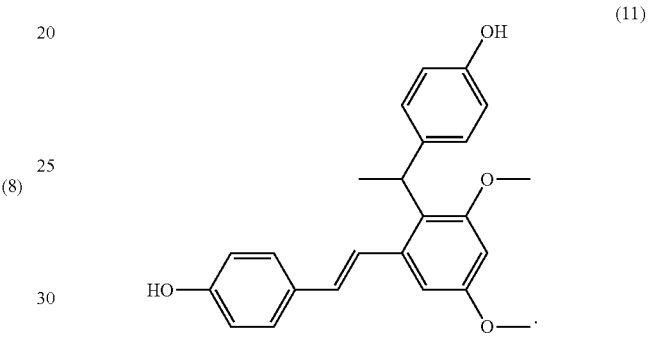
(11)

21. A novel hydroxystilbene derivative represented by Formula (12) or a pharmacologically permissible salt thereof:

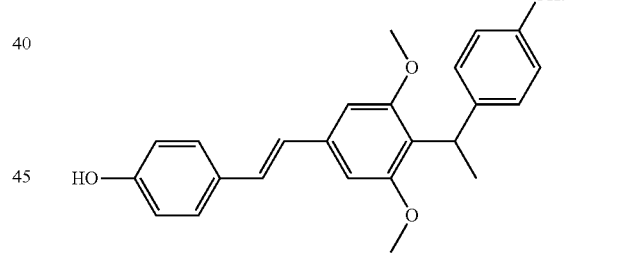
(12)

22. A novel hydroxystilbene derivative represented by Formula (13) or a pharmacologically permissible salt thereof:

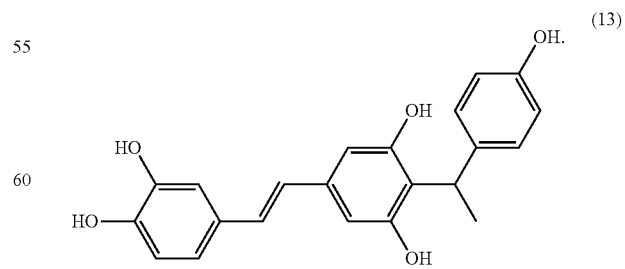
(13)

* * * * *